United States Patent [19]

Metzger et al.

[11] Patent Number: 4,515,789
[45] Date of Patent: May 7, 1985

[54] β-LACTAM ANTIBIOTICS

[75] Inventors: Karl G. Metzger; Wilfried Schröck; Dieter Häbich; Paul Naab, all of Wuppertal; Hans-Joachim Zeiler, Velbert, all of Fed. Rep. of Germany

[73] Assignee: Bayer Aktiengesellschaft, Leverkusen, Fed. Rep. of Germany

[21] Appl. No.: 483,062

[22] Filed: Apr. 7, 1983

[30] Foreign Application Priority Data

Apr. 22, 1982 [DE] Fed. Rep. of Germany ........ 3215085

[51] Int. Cl.³ .................. C07D 499/68; C07D 499/70; C07D 501/34; C07D 501/56
[52] U.S. Cl. .................. 514/196; 106/18.22; 260/239.1; 514/201; 514/202; 514/203; 514/206; 514/207; 514/210; 514/195; 426/335; 426/532; 544/22; 544/25; 544/27; 544/28; 544/90; 544/92; 544/359; 546/183; 548/178; 548/217; 548/318
[58] Field of Search ....................... 544/27, 28, 93, 90, 544/92, 22, 25, 359; 260/239.1; 424/246, 248.53, 250, 256, 271, 272, 274; 546/183; 548/178, 217, 318; 426/532

[56] References Cited
U.S. PATENT DOCUMENTS
4,200,576 4/1980 Feyen et al. ...................... 544/22

Primary Examiner—Paul M. Coughlan, Jr.
Attorney, Agent, or Firm—Sprung, Horn, Kramer & Woods

[57] ABSTRACT

A 3-β-(vic-dihydroxyphenylmethyleneamino-2-oxo-imidazolidine)- or 3-β-(vic-dihydroxyphenyl-methyleneamino-2,3-dioxo-piperazine)-1-carbonylamino-acetamidoazetidin-2-one having an acidic grouping on ₁N, e.g. of the formula

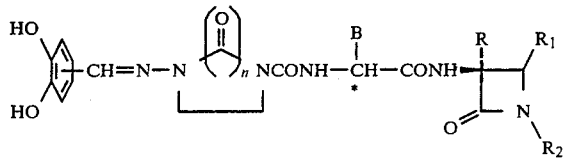

The compounds are antibiotically active, especially against Pseudomonas bacteria and can be used in combating bacterial infection, as a preservative and as a growth promoting agent in animal feeds.

18 Claims, No Drawings

β-LACTAM ANTIBIOTICS

The present invention relates to β-lactam antibiotics, processes for their preparation and their use as medicaments, in particular as antibacterial agents and as agents for promoting growth and for improving the utilization of feed in animals.

It has already been disclosed that certain α-(imidazolidin-2-oxo-1-yl-carbonylamino)-acetamidoazetidinone derivatives which carry a benzylideneamino substituent on the imidazolidinone ring exhibit high antibacterial activity (German Offenlegungsschrift 3,104,145 A₁, and U.S. Pat. Nos. 4,147,693 and 4,215,118.)

Surprisingly, the azetidinone derivatives which carry a β-(vic-dihydroxy-phenylmethyleneamino-2-oxoimidazolidine) or β-(vic-dihydroxy-phenylmethyleneamino-2,3-dioxo-piperazine)-1-carbonylamino-acetamido radical in the 3-position and an acidic group in the 1-position exhibit a substantially more powerful action against Pseudomonas bacteria than the benzylideneamino-imidazolidinone-acetamido-substituted β-lactams described and claimed in the abovementioned Offenlegungsschriften.

The present invention therefore relates to 3-β-(vic-dihydroxy-phenylmethyleneamino-2-oxo-imidazolidine- and -2,3-dioxo-piperazine-1-carbonylamino-acetamido)azetidin-2-ones having an acidic grouping on ₁N. An acidic grouping is also understood as meaning the group —C—COOE.

The preferred azetidinone derivatives of the invention of the general formula I

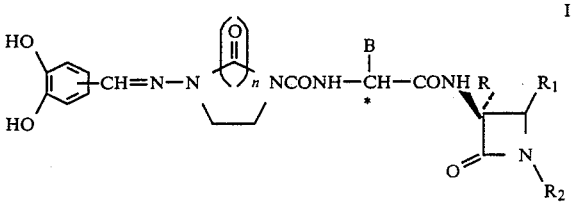

in which
B represents optionally substituted phenyl or cyclohexadienyl, or an unsaturated, optionally substituted heterocyclic ring;
R represents hydrogen or methoxy;
n is 1 or 2;
$R_1$ is hydrogen or optionally substituted alkyl;
$R_2$ is $SO_3^\ominus M^\oplus$ and
$M^\oplus$ is a proton or a cation;
or $R_1$ and $R_2$, together with the azetidinone ring to which they are bonded, represent

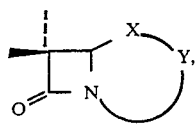

wherein
X represents S, O, SO, SO₂ or CH₂; and
Y represents the group

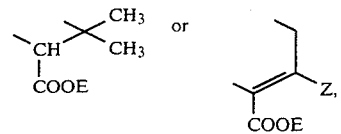

in which the carbon atom which carries the —COOE group is bonded to the nitrogen atom of the β-lactam ring, and Z represents hydrogen, halogen, alkoxy or —CH₂—T, T denotes hydrogen, alkyl—CO—O—, pyridinium, carboxamidopyridinium, aminopyridinium, carbamoyloxy, azido, cyano, hydroxyl, the group —S—phenyl which can be substituted, or the group —S—het, in which het represents an optionally substituted 5-membered or 6-membered heterocyclic ring;
and wherein
E represents hydrogen, a pharmaceutically usable ester grouping, a salt-forming cation or a suitable protective group;

and, with respect to the chirality center C, these compounds of the formula I can be present in the two possible R and S configurations, and as mixtures of the diastereomers resulting therefrom, and in respect of the imino group, the compounds of the formula I can be present both in the syn-form and anti-form, and these compounds of the formula I can also be present in the various hydrate forms.

Optionally substituted phenyl B is phenyl which can be monosubstituted or disubstituted by methyl, ethyl, aminomethyl, hydroxyl, methoxy, ethoxy, carbamoyloxy, acetoxy, amino, mesylamino, methylamino, aminosulphonylamino, guanidyl, carbamoylamino, carboxyl, methoxycarbonyl, carbamoyl, amidino, mesyl, methylsulphinyl, sulpho, methylthio or halogen.

An unsaturated, optionally substituted heterocyclic ring B may be any unsaturated 5-membered or 6-membered heterocyclic structure which has 1 to 4 heteroatoms, contains oxygen, nitrogen or sulphur atoms in the ring, and can be unsubstituted or monosubstituted or disubstituted by methyl, ethyl, hydroxyl, oxo, amino, imino, mesyl, mesylamino, carboxyl, carbamoyl or acetyl.

An unsaturated, optionally substituted heterocyclic ring B is preferably the furyl, methylfuryl, thienyl, methylthienyl, 2-aminothiazolyl, thiazolyl, methylisoxazolyl, isoxazolyl, pyridyl, 2-aminopyrimidyl, thiadiazolyl, pyranyl, thiapyranyl or sydnonyl group.

Optionally substituted alkyl $R_1$ is straight-chain or branched alkyl which preferably has up to 5 C atoms, may be unsaturated or cyclized, and can be substituted by hydroxyl, amino, carboxyl, carbamoyl or mesyl.

The cation $M^\oplus$ or E may be any pharmaceutically usable cation. Alkali metal cations and alkaline earth metal cations, the aluminum cation and the ammonium ion can be employed as inorganic cations, and protonated organic amines, such as primary, secondary and tertiary aliphatic amines and heterocyclic amines, can be employed as organic cations. The following may be mentioned as examples: di- and tri-(lower alkyl)-amines, for example diethylamine, triethylamine, aminoethanol, tri-β-hydroxyethylamine, procaine, dibenzylamine, N,N'-dibenzylethylenediamine, N-benzyl-β-phenylethylamine, N-methyl- and N-ethylmorpholine, 1- ephenamine, dehydroabietylamine, N,N'-bis-dehydroabietylethylenediamine and N-(lower alkyl)-piperidine. So-called basic amino acids, such as lysine or arginine, in protonated form, can also be used as cations. The sodium ion is particularly preferred.

Alkoxy Z is preferably methoxy, ethoxy, n-propoxy and i-propoxy.

Alkyl-COO T is preferably acetate, propionate, n-butyrate and i-butyrate, which can be substituted by carboxyl, hydroxyl or amino. Preferred substituents of the —S—phenyl group T are methyl, halogen, amino, hydroxyl and carboxyl.

Optionally substituted 5-membered or 6-membered heterocyclic rings for T=—S—het are all 5-membered or 6-membered heterocyclic structures which have 1-4 heteroatoms, contain oxygen, nitrogen or sulphur atoms in the ring, and can be unsubstituted or monosubstituted or disubstituted by alkyl which can be substituted by carboxyl, sulpho, amino, methylamino, dimethylamino or hydroxyl and has up to 3 C atoms, or by hydroxyl, oxo, amino, imino or sulpho.

Optionally substituted 5-membered or 6-membered heterocyclic rings in T=—S—het are preferably the thiazole, isothiazole, thiadiazolyl, triazolyl or tetrazolyl ring, each of which is unsubstituted or substituted by methyl, sulphomethyl, carboxymethyl or dimethylaminoethyl, or are the pyridyl, 1-oxidopyridyl, 2-methyl-5-oxo-6-hydroxy-1,4-dihydro-1,2,4-triazine and the 4-formylmethyl-5-oxo-6-hydroxy-4,5-dihydro-1,2,4-triazine ring.

Suitable pharmaceutically usable ester groups E are those ester groups which, like the pivaloyloxymethyl, the ethoxycarbonyloxyethyl or the phthalidyl group, are cleaved under physiological conditions.

Suitable protective groups E are all protective groups used in β-lactam antibiotic chemistry, such as for example, the silyl, boryl, phosphonyl, phosphatyl, acyl, alkoxycarbonyl, benzyl, 2-acetoacetyl, t-butyl and benzhydryl groups, and those β-substituted ethyl groups which are cleaved into fragments by nucleophilic or electrophilic agents, such as, for example, the β-silylethyl or β-halogenoethyl group.

All crystalline forms and hydrate forms of the compounds according to the invention, and their salts, are antibacterially effective in the same manner.

Furthermore, it has been found that the compounds according to the invention are obtained by a process in which 3-(amino-acetamido)-azetidin-2-ones having an acidic grouping on $_1$N, in their acid form or as salts with suitable cations or in a form in which the acidic group is protected, are reacted with compounds of the general formula II

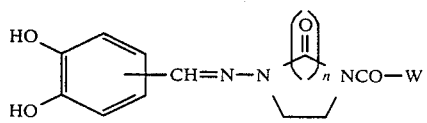

in which
W represents halogen, azide or another suitable nucleofugic leaving group, and n is 1 or 2, and in which the two hydroxyl groups can be protected by silyl or cyclosilyl groups,
in the presence of a solvent and, if appropriate, of an acid-binding agent, at temperatures from about −20° C. to about +50° C., and the β-lactam antibiotics obtained are freed, if appropriate, from the protective groups present, and if appropriate are converted into their pharmaceutically usable salts or esters, or, if desired, the free acids are prepared from the salts obtained.

3-(Amino-acetamido)-azetidin-2-ones which have an acidic grouping on $_1$N and are preferably employed in the process are compounds of the general formula III

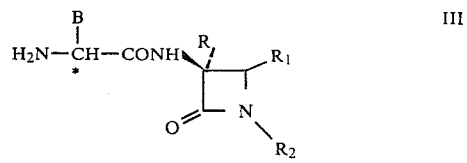

in which
B, R, $R_1$, $R_2$ and C have the meanings given above.

Suitable diluents in the process according to the invention are water and all inert organic solvents, preferably those which are miscible with water. These include, in particular, lower dialkyl ketones, for example acetone and methyl ethyl ketone; cyclic ethers, for example tetrahydrofuran and dioxane; nitriles, for example acetonitrile; lower dialkylformamides, for example dimethylformamide; lower alkyl alcohols, for example ethanol and isopropanol, and dimethylsulphoxide. These solvents can also be used in the form of mixtures with one another, and in the form of any desired mixture of one or more of these solvents with water. The process according to the invention can thus be carried out in the presence of: (a) exclusively water, (b) exclusively one or more organic solvents. If, due to the presence of water, it is possible to carry out a pH measurement during the reaction according to the invention, the pH of the reaction mixture is preferably kept between 6.5 and 7.5 by the addition of bases or by the use of buffer mixtures. The process according to the invention can, however, also be very readily carried out in another pH range, for example between 4.5 and 9.0, or at pH 2.0 and 4.5. Furthermore it is possible to carry out the reaction in solvents which are immiscible with water, for example halogenated hydrocarbons, such as chloroform or methylene chloride, with the addition of organic bases, preferably lower alkylamines, for example triethylamine or diethylamine, or of cyclic bases, for example N-ethylpiperidine. Furthermore, it is possible to carry out the reaction in a mixture of water and a water-immiscible solvent, such as, for example, lower alkyl ethers, such as diethyl ether, halogenated hydrocarbons, such as chloroform and methylene chloride; carbon disulphide, isobutyl methyl ketone; esters, such as ethyl acetate; aromatic hydrocarbons, such as benzene, it being advantageous to stir the mixture vigorously and to keep the pH value between 4.5 and 9.0 or, for example, 2.0 and 4.5, by the addition of bases or the use of customary buffer solutions, for example a phosphate, acetate or citrate buffer. However, the reaction can also be carried out in water alone, in the absence of organic solvents, in the presence of an organic or inorganic base or with the addition of customary buffer substances.

All acid binders customarily used in antibiotic chemistry may be used as acid-binding agents. These include inorganic bases and organic bases which are difficult to acylate, for example, because of steric hindrance. Sodium hydroxide and potassium hydroxide may be mentioned as examples of inorganic bases. Suitable organic bases are virtually all open-chain or cyclic amines which can be acylated only with difficulty, if at all, and also heteroaromatic bases. Tertiary amines, preferably lower alkylamines, for example triethylamine, and/or cyclic bases, for example pyridine, may be mentioned as examples of bases, and dicyclohexylamine may be mentioned as an example of a secondary amine which is difficult to acylate.

In the process according to the invention, it is necessary to add a base only when acidic compounds are formed during reaction, for example in the case in which W represents halogen or azide.

The reaction temperatures can be varied within a relatively wide range. In general, the reaction is carried out at between about $-20°$ C. and about $+50°$ C., preferably between $0°$ and $+20°$ C. However, as in the case of most chemical reactions, it is also possible in principle to employ higher or lower temperatures.

The reaction can be carried out under atmospheric pressure, but also under reduced or elevated pressure. In general, the reaction is carried out under atmospheric pressure.

In carrying out the process according to the invention, the proportions of the 3-(amino-acetamido)-azetidin-2-ones having an acidic grouping on $_1$N and the compounds of the general formula II can be varied within wide limits, without the result being disadvantageously affected. The starting materials can, for example, be brought to reaction with one another in equimolar amounts. However, it may be advantageous to use one of the two reactants in excess in order to facilitate the purification of the desired β-lactam antibiotic or its preparation in pure form, and to increase the yield.

The amount of the bases which may be used is determined, for example, by the desire to maintain a particular pH value. Where a pH measurement and adjustment is not carried out, or is not possible owing to the lack of sufficient amounts of water in the diluent, or is not relevant, it is preferable to add 2 mol equivalents of base.

Working up the reaction mixtures to prepare the compounds according to the invention, and their salts, is carried out in every case in the manner generally known for these substances. The isolation and purification of the compounds according to the invention, and the liberation of the free acids from the salts or the conversion of the free acids into salts, are also carried out by generally customary methods of organic chemistry, these methods being known to any skilled worker.

3-(Amino-acetamido)-azetidin-2-ones which have an acidic grouping on $_1$N and are used as starting materials are already known, and are obtainable by known methods; all crystalline forms, hydrate forms and salts of these compounds are suitable starting materials for the process according to the invention.

The compounds of the general formula II which are used as starting materials can be obtained, for example, by the following route:

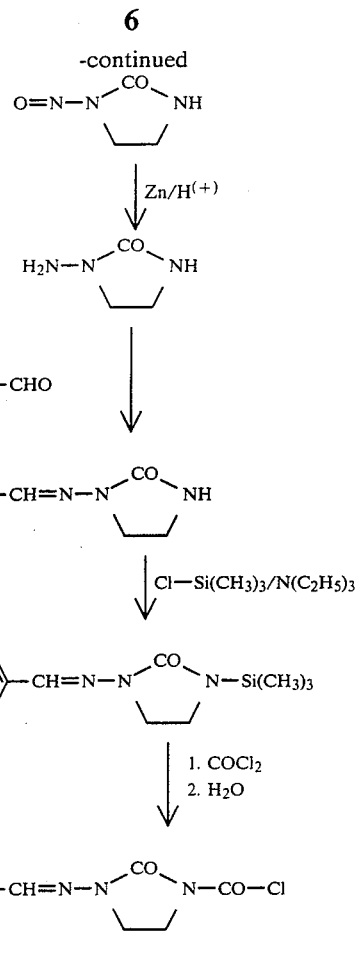

The phosgenation is also possible without prior silylation, in an inert organic solvent, in the presence of a base. Those compounds of the general formula II, in which W is azide, are obtained in a customary manner, for example from the corresponding compounds II, in which W is halogen, by reaction, for example, with alkali metal azides.

Furthermore, it has been found that the compounds according to the invention are obtained by a process in which 3-aminoazetidin-2-ones having an acidic grouping on $_1$N are reacted with a (vic-dihydroxyphenylmethyleneamino-(2-oxo-imidazolidine)- or -(2,3-dioxo-piperazine)-1-carbonylamino-acetic acid derivative which acts as an acylating agent, and, if appropriate after any protective groups present have been split off, the products are converted into pharmaceutically usable salts or esters, or, if desired, the free acids are prepared from the salts obtained.

In the processes, compounds of the general formula IV

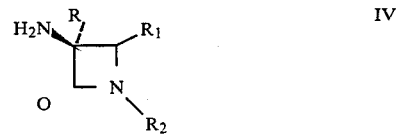

in which
R, R$_1$ and R$_2$ have the meanings given above, are preferably employed as 3-aminoazetidin-2-ones having an acidic grouping on ₁N, and those of the general formula V

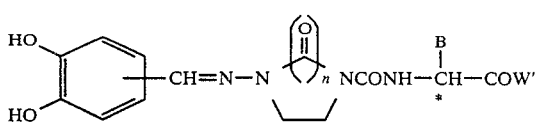

in which
n, B and C have the meanings given above and
W' is OH or a reactive leaving group, are preferably employed as derivatives of a (vic-dihydroxyphenylmethylamino)-(2-oxo-imidazolidin-1-yl) or -(2,3-dioxo-piperazin-1-yl)-carbonylaminoacetic acid which act as acylating agents. Examples of suitable compounds (V) are free acids, acid halides, acid anhydrides, active esters, active amides and ketenes with the desired acyl radical. The acylation can, if appropriate, be carried out in the presence of a base, such as triethylamine, tributylamine, pyridine or sodium bicarbonate, molecular sieves, carbodiimides, for example dicyclohexyl carbodiimide, epoxides, for example propylene oxide or butylene oxide, or enzymes. The reaction can be carried out by the acid chloride, acid anhydride, carbodiimide or active ester method.

Examples of suitable solvents for these reactions are ethers and cyclic ethers, such as tetrahydrofuran, ketones, such as acetone, amides, such as dimethylformamide, and chlorinated hydrocarbons, such as chloroform, in the presence or absence of water, depending on the sensitivity of the COW' group to hydrolysis.

3-Aminoazetidin-2-ones which have an acidic grouping on ₁N and are used as starting materials are already known, and are obtainable by known methods, and all crystalline forms, hydrate forms and salts of these compounds are suitable starting materials for the process according to the invention.

The compounds of the general formula V which are used as starting materials and in which W' is a relative leaving group are obtained from the compounds of the general formula V, in which W' is OH, by reaction with activating agents, such as inorganic or organic acid halides or acid anhydrides, or by condensation to give activated esters, amides or hydroxylamides, for example by means of carbodiimides.

The compounds of the general formula V which are used as starting materials and in which W' is OH are obtained from the compounds of the general formula II and amino acids.

Furthermore, it has been found that compounds according to the invention, of the general formula VI

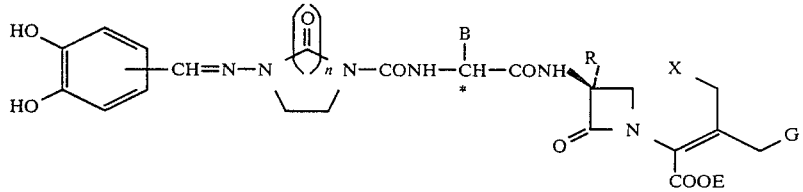

in which
n, B, C, R, X and E have the above meanings and
T' has the meaning of T given above, with the exception of hydrogen,
are obtained by a process in which compounds of the general formula VII

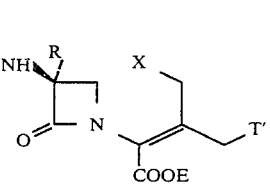

in which
n, B, C, R, X and E have the meanings given above and G denotes a nucleofugic group, such as halogen,
pseudohalogen, acetoxy, dichloroacetoxy or mesyloxy,
are brought to reaction with a nucleophile [T']⁻, in which T' has the meaning given above, [G]⁻ being eliminated, and, if appropriate after any protective groups present have been split off, the products are converted into the pharmaceutically usable salts or esters, or, if desired, the free acids are prepared from the salts obtained.

Depending on the nucleofugic reactivity of G, different temperatures are required for this process; thus, for example, compounds of the general formula VII in which G=halogen or mesyloxy can even be reacted at below 0° or at room temperature, while when G is, for example, acetoxy, temperatures above 50° C. to 120° C. are required in most cases.

The compounds of the general formula VII, which are used as starting materials for the process according to the invention, are prepared from the compounds of the general formula V and compounds of the general formula XI

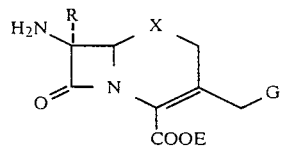

in which

R, E, X and G have the meanings given above, and which are already known and are obtainable by known methods, or from compounds of the general formula II and compounds of the general formula XII

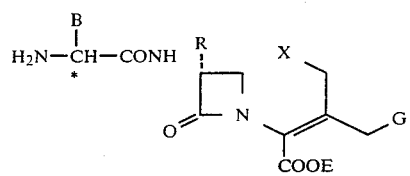

XII in which
B, C, R, X, E and G have the meanings given above, or from compounds of the general formula VII, in which G is OH.

The following may be mentioned as examples of new β-lactam antibiotics according to the invention (formula VIII-X):

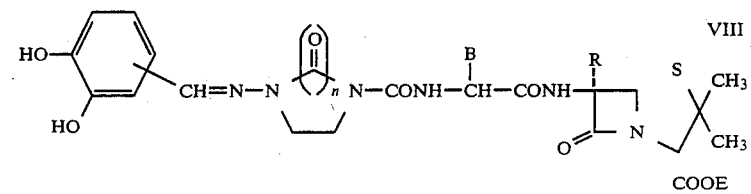

VIII

| Position of the vicinal OH groups | n | B | R | E |
|---|---|---|---|---|
| 2,3 | 1 | ![phenyl] | H | H |
| " | 1 | " | OCH₃ | H |
| " | 1 | " | H | —CH₂OCOC(CH₃)₃ |
| 3,4 | 1 | " | H | H |
| " | 1 | " | OCH₃ | H |
| " | 1 | " | H | —CH(CH₃)—OCOOC₂H₅ |
| 2,3 | 2 | " | H | H |
| " | 1 | HO-C₆H₄- | H | H |
| " | 1 | " | OCH₃ | H |
| " | 1 | m-HO-C₆H₄- | H | H |
| " | 1 | 3,4-(HO)₂-C₆H₃- | H | H |
| 3,4 | 1 | HO-C₆H₄- | H | H |
| " | 1 | " | —OCH₃ | H |

-continued
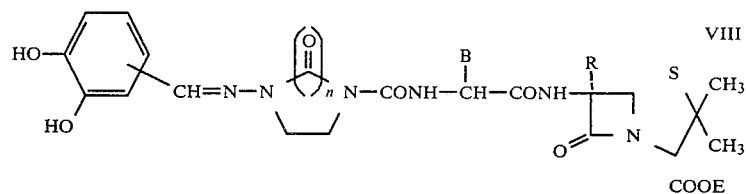
| Position of the vicinal OH groups | n | B | R | E |
|---|---|---|---|---|
| " | 1 | 3-hydroxyphenyl | H | H |
| " | 1 | 3,4-dihydroxyphenyl | H | H |
| " | 1 | 2-thienyl | H | H |
| " | 1 | " | OCH₃ | H |
| " | 1 | " | H | 3-(1-methylethyl)-1(3H)-isobenzofuranonyl |
| 2,3 | 1 | " | H | H |
| " | 1 | 2-furyl | H | H |
| 3,4 | 1 | " | H | H |
| " | 1 | 2-aminothiazol-4-yl | H | H |
| 2,3 | 1 | " | H | H |
| " | 1 | " | —OCH₃ | H |
| " | 1 | 4-aminophenyl | H | H |
| " | 1 | 3-aminophenyl | H | H |
| 3,4 | 1 | " | H | H |

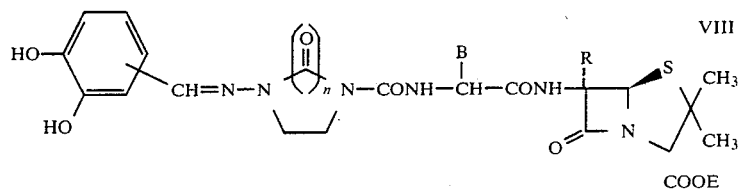
| Position of the vicinal OH groups | n | B | R | E |
|---|---|---|---|---|
| " | 1 | H₂N—⟨C₆H₄⟩— | H | H |
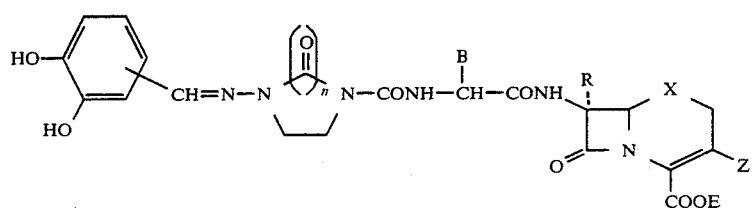
| Position of the vicinal OH groups | n | B | R | X | Z | E |
|---|---|---|---|---|---|---|
| 2,3 | 1 | —C₆H₅ | H | S | —CH₂OCOCH₃ | H |
| " | 1 | " | H | S | " | —CH₂OCOC(CH₃)₃ |
| " | 1 | " | —OCH₃ | S | " | H |
| " | 2 | " | H | S | " | H |
| " | 1 | " | H | —SO— | " | H |
| " | 1 | " | H | —SO₂— | " | H |
| " | 1 | " | H | —O— | " | H |
| " | 1 | " | —OCH₃ | —O— | " | H |
| " | 1 | " | H | —CH₂— | " | H |
| " | 1 | " | H | —S— | —CH₂—S—(thiadiazole-CH₃) | H |
| " | 1 | " | H | —S— | —CH₂—S—(tetrazole-N-CH₃) | H |
| " | 1 | " | H | —O— | " | H |
| " | 1 | " | —OCH₃ | —O— | " | H |
| " | 1 | " | H | —S— | —Cl | H |
| " | 1 | " | H | —S— | —OCH₃ | H |
| " | 1 | " | H | —S— | —CH₃ | H |
| " | 1 | " | H | —S— | —CH₂—S—(triazole) | H |
| " | 1 | " | H | —S— | —CH₂—S—(CH₃-triazine-OH,=O) | H |

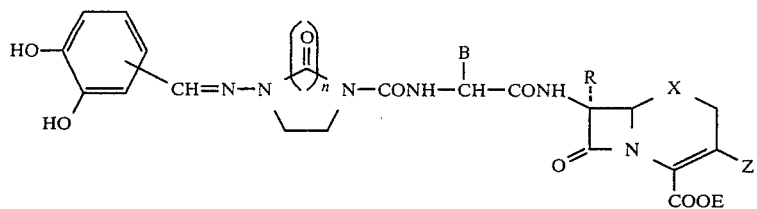
| Position of the vicinal OH groups | n | B | R | X | Z | E |
|---|---|---|---|---|---|---|
| " | 1 | " | H | —S— | —CH$_2$—S— (tetrazole with N-CH$_2$CH$_2$-N) | |
| " | 1 | " | H | —S— | —CH$_2$— (1,2,4-triazine with OH, =O, CHO) | H |
| " | 1 | " | H | —S— | —CH$_2$—⊕N(pyridinium) | H |
| " | 1 | " | H | —S— | —CH$_2$—⊕N(pyridinium)—CONH$_2$ | H |
| " | 1 | " | H | —O— | —CH$_2$—S—(thiadiazole)—CH$_3$ | H |
| " | 1 | " | —OCH$_3$ | —O— | —Cl | H |
| " | 1 | " | H | —O— | —OCH$_3$ | H |
| " | 1 | " | —OCH$_3$ | —O— | —CH$_3$ | H |
| " | 2 | " | H | —O— | —CH$_2$— (triazole) | H |
| " | 1 | " | —OCH$_3$ | —O— | —CH$_2$—S— (N-CH$_3$ triazine with OH, =O) | H |
| " | 1 | " | H | —O— | —CH$_2$—S— (tetrazole with N-CH$_2$CH$_2$-N) | H |

-continued
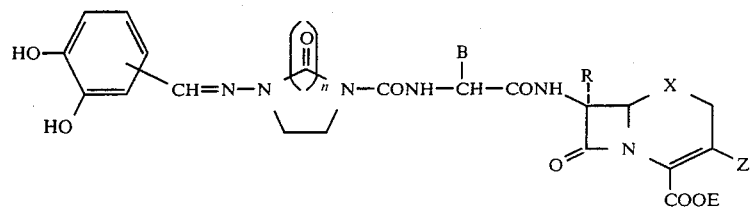
IX
| Position of the vicinal OH groups | n | B | R | X | Z | E |
|---|---|---|---|---|---|---|
| " | 1 | " | —OCH₃ | —O— | -CH₂-S-triazine-CHO | H |
| " | 1 | " | H | —O— | —CH₂—N⊕(pyridinium) | H |
| " | 1 | " | —OCH₃ | —O— | —CH₂—⊕N(pyridinium)-CONH₂ | H |
| " | 1 | " | H | —O— | —CH₂—S-tetrazole-N-SO₃⊖ | H |
| " | 1 | " | —OCH₃ | —S— | " | H |
| 3,4 | 1 | " | H | S | —CH₂OCOCH₃ | H |
| " | 1 | " | H | S | " | —CH₂OCOC(CH₃)₃ |
| " | 1 | " | —OCH₃ | S | " | H |
| " | 2 | " | H | S | " | H |
| " | 1 | thiophene | H | —SO— | " | H |
| " | 1 | thiophene | H | —SO₂— | " | H |
| " | 1 | furan | H | —O— | " | H |
| " | 1 | aminothiazole | H | —O— | " | H |
| " | 1 | HO-phenyl | —OCH₃ | —O— | " | H |
| " | 1 | HO-phenyl | H | —CH₂— | " | H |

-continued
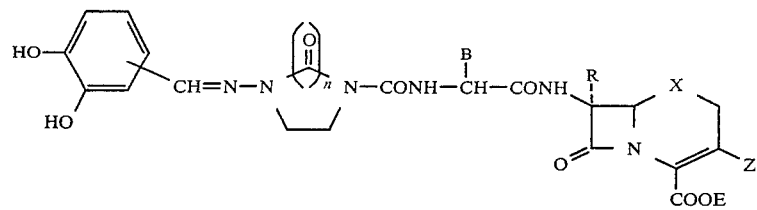
IX
| Position of the vicinal OH groups | n | B | R | X | Z | E |
|---|---|---|---|---|---|---|
| " | 1 | 3,4-dihydroxyphenyl | H | —S— | —CH₂—S-[1,3,4-thiadiazol-2-yl with CH₃] | H |
| " | 1 | 4-aminophenyl | H | —S— | —CH₂—S-[1-methyltetrazol-5-yl] | H |
| " | 1 | 4-aminophenyl | H | —O— | " | H |
| " | 1 | phenyl | —OCH₃ | —O— | " | H |
| " | 1 | 4-hydroxyphenyl | H | —S— | —Cl | H |
| " | 1 | 3-hydroxyphenyl | H | —S— | —OCH₃ | H |
| " | 1 | 3,4-dihydroxyphenyl | H | —S— | —CH₃ | H |
| " | 1 | 4-aminophenyl | H | —S— | —CH₂—S-[1H-1,2,3-triazol-4-yl] | H |
| " | 1 | 3-aminophenyl | H | —S— | —CH₂—S-[4-methyl-5-hydroxy-6-oxo-1,2,4-triazin-3-yl] | H |

-continued

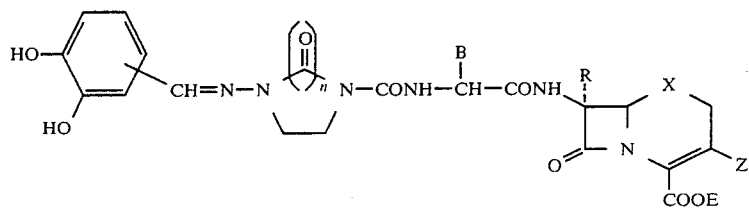

IX

| Position of the vicinal OH groups | n | B | R | X | Z | E |
|---|---|---|---|---|---|---|
| " | 1 | thien-2-yl | H | —S— | —CH₂—S-(1-(2-dimethylaminoethyl)tetrazol-5-yl) | H |
| " | 1 | phenyl | H | —S— | —CH₂-(6-hydroxy-4-(2-oxoethyl)-5-oxo-4,5-dihydro-1,2,4-triazin-3-yl) | H |
| " | 1 | 3-thienyl | H | —S— | —CH₂—⊕N-pyridinium | H |
| " | 1 | fur-2-yl | H | —S— | —CH₂—⊕N-(4-carbamoylpyridinium) | H |
| " | 1 | 2-aminothiazol-4-yl | H | —O— | —CH₂—S-(5-methyl-1,3,4-thiadiazol-2-yl) | H |
| " | 1 | 6-amino-pyridin-2-yl | —OCH₃ | —O— | —Cl | H |
| " | 1 | 2-aminopyrimidin-4-yl | H | —O— | —OCH₃ | H |
| " | 1 | phenyl | —OCH₃ | —O— | —CH₃ | H |
| " | 2 | 4-hydroxyphenyl | H | —O— | —CH₂-(1H-1,2,3-triazol-4-yl) | H |

-continued

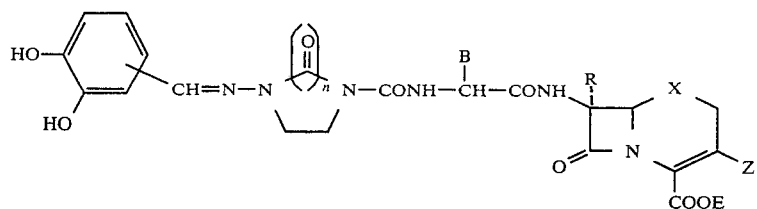

IX

| Position of the vicinal OH groups | n | B | R | X | Z | E |
|---|---|---|---|---|---|---|
| " | 1 | 3-hydroxyphenyl | —OCH₃ | —O— | —CH₂—S-(triazine with CH₃, N—N, OH, =O) | H |
| " | 1 | 3,4-dihydroxyphenyl | H | —O— | —CH₂—S-(tetrazole with CH₂CH₂N(CH₃)—) | H |
| " | 1 | 4-aminophenyl | —OCH₃ | —O— | —CH₂—S-(triazine with OH, =O, N-CH₂CHO) | H |
| " | 1 | 3-aminophenyl | H | —O— | —CH₂—N⁺(pyridinium) | H |
| " | 1 | 2-amino-4-methylthiazol-5-yl | —OCH₃ | —O— | —CH₂—⁺N(pyridinium)-CONH₂ | H |
| " | 1 | 2-aminopyrimidin-methyl | H | —O— | —CH₂—S-(tetrazole with N-CH₂SO₃⁻) | H |
| " | 1 | 2-thienyl | —OCH₃ | —S— | " | H |

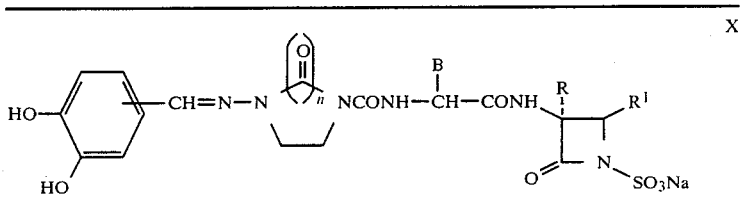
| Position of the vicinal OH groups | n | B | R | $R_1$ |
|---|---|---|---|---|
| 2,3 | 1 |  | H | H |
| " | 2 | " | H | H |
| " | 1 | " | —OCH$_3$ | H |
| " | 1 | " | —H | α-CH$_3$ |
| " | 1 | " | —H | β-CH$_3$ |
| " | 1 | " | —H | α-C$_2$H$_5$ |
| " | 1 | " | —H | β-C$_2$H$_5$ |
| " | 1 | " | —H | α-CH$_2$OH |
| " | 1 | " | —H | β-CH$_2$OH |
| " | 1 | " | —H | α-CH$_2$COOH |
| " | 1 | " | —H | β-CH$_2$COOH |
| " | 1 | " | —H | α-CH$_2$NH$_2$ |
| 3,4 | 1 | " | —H | —H |
| " | 2 | " | —H | —H |
| " | 1 | " | —OCH$_3$ | —H |
| " | 1 | 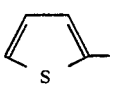 | —H | α-CH$_3$ |
| " | 1 |  | —H | β-CH$_3$ |
| " | 1 | 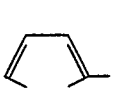 | —H | α-C$_2$H$_5$ |
| " | 1 | 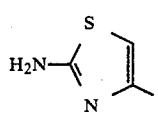 | —H | β-C$_2$H$_5$ |
| " | 1 | 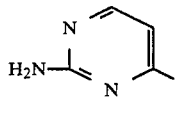 | —H | α-CH$_2$OH |
| " | 1 | 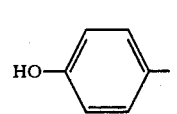 | —H | β-CH$_2$OH |
| " | 1 | 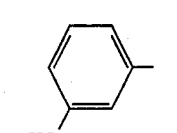 | —H | α-CH$_2$COOH |

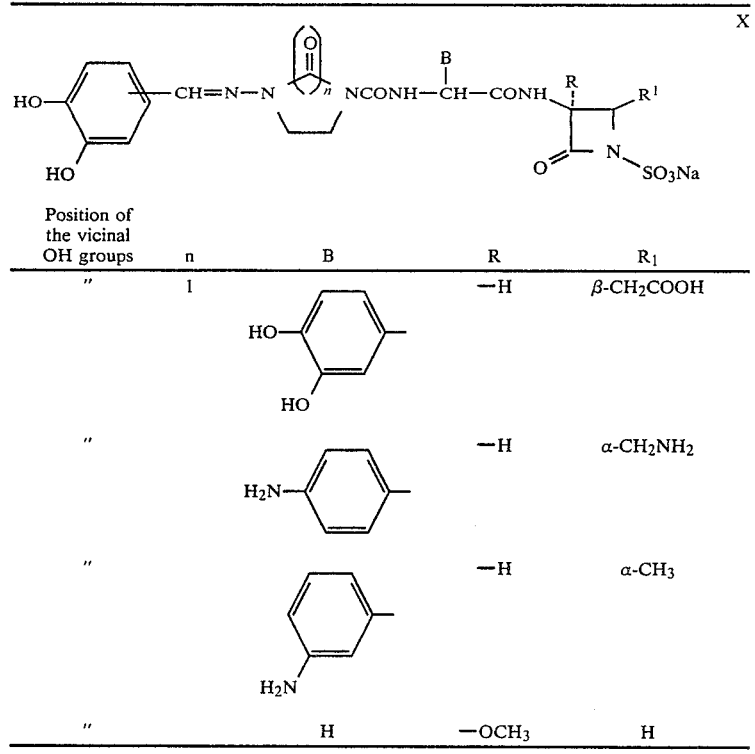

| Position of the vicinal OH groups | n | B | R | R₁ |
|---|---|---|---|---|
| " | 1 | HO-C₆H₃(OH)- | —H | β-CH₂COOH |
| " |  | H₂N-C₆H₄- | —H | α-CH₂NH₂ |
| " |  | H₂N-C₆H₄- | —H | α-CH₃ |
| " |  | H | —OCH₃ | H |

The compounds according to the invention, in the form of the free acid, in crystalline as well as amorphous forms, and in anhydrous form as well as in various hydrate forms; have the same antibacterial action. Likewise, these compounds in the form of their salts, for example sodium salts, in crystalline as well as amorphous forms, and in anhydrous as well as hydrous forms, for example as the hydrate, have the same antibacterial action.

The compounds according to the invention exhibit a broad antibacterial action, that is to say an action against several families of bacteria in the Gram-negative and Gram-positive range, and against β-lactamase formers, in addition to exhibiting good toleration and solubility. Owing to their powerful antibacterial properties, and because of their ability to improve the growth and the feed utilization in animals, the compounds according to the invention thus represent an enrichment of the art.

The compounds according to the invention exhibit a powerful antimicrobial activity, coupled with low toxicity and good toleration. These properties enable them to be used as active compounds in medicine, and also as substances for preserving inorganic and organic materials, in particular organic materials of all kinds, for example polymers, lubricants, paints, fibers, leather, paper and timber, and foodstuffs and water.

The active compounds according to the invention are active against a very broad spectrum of microorganisms. With their aid, it is possible, for example, to combat Gram-negative and Gram-positive bacteria and bacteria-like microorganisms, and to prevent, alleviate and/or cure diseases caused by these pathogens.

The active compounds according to the invention are particularly active against bacteria and bacteria-like microorganisms. They are therefore particularly suitable, in human medicine and veterinary medicine, for the prophylaxis and chemotherapy of local and systemic infections caused by these pathogens.

For example, local and/or systemic diseases which are caused by the following pathogens or by mixtures of the following pathogens can be treated and/or prevented:

Micrococcaceae, such as Staphylococci, for example Staphylococcus aureus, Staph. epidermidis, Staph. aerogenes and Gaffkya tetragena (Staph. = Staphylococcus); Lactobacteriaceae, such as Streptococci, for example Streptococcus pyogenes, α- and β-haemolysing Streptococci, non-(γ-)-haemolysing Streptococci, Str. viridans, Str. faecalis (Enterococci), Str. Agalactiae, Str. lactis, Str. equi and Str. anaerobis, and Diplococcus pneumoniae (Pneumococci) (Str. = Streptococci);

Neisseriaceae, such as Neisseriae, for example Neisseria gonorrhoeae (Gonococci), N. meningitidis (Meningococci), N. catarrhalis and N. flava (N. = Neisseria);

Corynebacteriaceae, such as Corynebacteria, for example Corynebacterium diphtheriae, C. pyogenes, C. diphtheroides, C. acnes, C. parvum, C. bovis, C. renale, C. ovis and C. murisepticum; Listeria bacteria, for example Listeria monocytogenes, Erysipelothrix bacteria, for example Erysipelothrix insidiosa; Kurthia bacteria, for example Kurthia zopfii (C. = Corynebacterium);

Enterobacteriaceae, such as Escherichiae bacteria of the Coli group, Escherichia bacteria, for example Escherichia coli, Enterobacter bacteria, for example E. aerogenes and E. cloacae, Klebsiella bacteria, for example K. pneumoniae and K. ozaenae, Erwiniae, for example Erwinia spec., Serratia, for example Serratia marcescens (E. = Enterobacter) (K. = Klebsiella), Proteae bacteria of the Proteus group, Proteus, for example Proteus vulgaris, Pr. morganii, Pr. rettgeri and Pr. mirabilis (Pr.=Proteus), and Providencia, for example Providencia sp., Salmonelleae, Salmonella bacteria, for example *Salmonella paratyphi* A and B, S. typhi, S. enteritidis, S. cholerae suis and *S. typhimurium* (S.=Salmonella), and Shigella bacteria, for example Shigella dysenteriae, *Sh. ambigua, Sh. flexneri, Sh. boydii* and *Sh. sonnei* (Sh.=Shigella);

Pseudomonadeceae, such as Pseudomonas bacteria, for example Pseudomonas aeruginosa and Ps. pseudomalleri (Ps.=Pseudomonas); Aeromonas bacteria, for example Aeromonas liquefaciens and *A. hydrophile* (A.-=Aeromonas); Spirillaceae, such as Vibrio bacteria, for example *Vibrio cholerae, V. proteus* and V. fetus (V.=Vibrio), Spirillum bacteria, for example *Spirillum minus;*

Parvobacteriaceae or Brucellaceae, such as Pasteurella bacteria, for example Pasteurella multocida, and Past. pestis (Yersinia), Brucella bacteria, for example Brucella abortus, *Br. melitensis* and Br. suis (Br.=Brucella), Haemophilus bacteria, for example *Haemophilus influenzae, H. ducreyi, H. suis, H. canis* and *H. aegypticus* (H.=Haemophilus), Bordetella bacteria, for example *Bordetella pertussis* and *B. bronchiseptica* (B.=Bordetella), Moraxella bacteria, for example *Moraxella lacunata;*

Bacterioidaceae, such as Bacteroides bacteria, for example *Bacteroides fragilis* and *B. serpens* (B.=Bacteroides), Fusiforme bacteria, for example *Fusobacterium fusiforme* and Sphaerophorus bacteria, for example *Sphaerophorus necrophorus, Sph. necroticus* and *Sph. pyrogenes* (Sph.=Sphaerophorus);

Bacillaceae, such as aerobic spore-forming Bacillaceae, for example *Bacillus anthracis, B. subtilis* and *B. cereus* (B.=Bacillus), and anaerobic spore-forming Chlostridia, for example *Clostridium perfringens, Cl. septicium, Cl. oedematiens, Cl. histolyticum, Cl. tetani* and *Cl. botulinum* (Cl.=Clostridium);

Spirochaetaceae, such as Borrelia bacteria, for example *Borrelia recurrentia* and *B. vincentii* (B.=Borrelia), Treponema bacteria, for example *Treponema pallidum, Tr. pertinue* and *Tr. carateum* (Tr.=Treponema), Leptospira bacteria and *Leptospira interrogans,* for example *Leptospira icterohaemorrhagiae, L. canicola, L. grippotyphosa, L. pomona, L. mitis* and *L. bovis* (L.=Leptospira).

The above list of pathogens is purely illustrative and is in no way to be interpreted as restrictive.

The active compounds according to invention are very particularly active against Pseudomonadaceae, as can be seen from the table below:

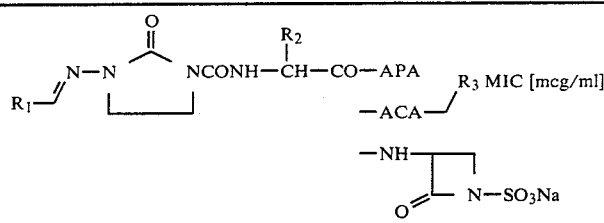

| Compound from Example no. | $R_1$ | $R_2$ | | $R_3$ | Psdm. W | Psdm. F41 |
|---|---|---|---|---|---|---|
| 7c | 2,3-dihydroxyphenyl (HO, HO) | phenyl | APA | — | ≦0.25 | ≦0.25 |
| 4 | 3,4-dihydroxyphenyl (HO, HO) | 4-hydroxyphenyl (HO—) | APA | — | 0.5 | ≦0.25 |
| 14b | " | " | ACA | —OCOCH$_3$ | 0.5 | 0.25 |
| 2d | " | phenyl | " | —S–(1-methyl-tetrazol-5-yl-thio) | ≦0.25 | 0.25 |
| 15 | " | 4-hydroxyphenyl (HO—) | " | " | 0.25 | ≦0.12 |
| 16b | 2,3-dihydroxyphenyl (HO, HO) | " | " | —OCOCH$_3$ | 0.25 | 0.25 |

-continued

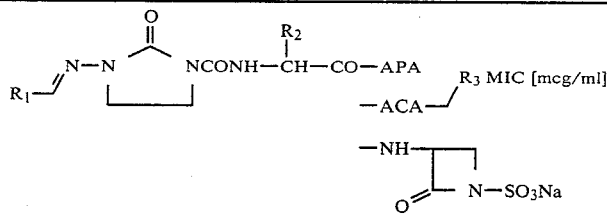

| Compound from Example no. | R₁ | R₂ | R₃ | | Psdm. W | Psdm. F41 |
|---|---|---|---|---|---|---|
| 17 | " | " | " | $-S-\overset{N=\!=\!=N}{\underset{\underset{CH_3}{N-N}}{\|}}$ | ≦0.25 | ≦0.25 |
| 23 | HO-, HO- (dihydroxyphenyl) | phenyl | $-N(H)-\overset{O}{\underset{\|}{C}}-\text{azetidinone-}N\text{-SO}_3Na$ | — | 4 | — |
| — | HO- (p-hydroxyphenyl) | " | APA | — | 8 | 8 |
| — | HO-, -OH (3,4-dihydroxyphenyl) | " | " | — | 64 | 64 |
| — | -OH, -OH (2,4-dihydroxyphenyl) | " | " | — | 16 | 16 |
| — | | | azlocillin | | 8 | 8 |
| — | | | cefsulodin | | 2 | 2 |
| — | | | moxalactam | | 8–16 | 32 |

Examples which may be mentioned of diseases which can be prevented, alleviated and/or cured by the active compounds according to the invention are: diseases of the respiratory passages and of the pharyngeal cavity; otitis; pharyngitis; pneumonia; peritonitis; pyelonephritis; cystitis; endocarditis; systemic infections; bronchitis; and arthritis.

The present invention includes pharmaceutical formulations which, in addition to non-toxic, inert pharmaceutically suitable excipients, contain one or more active compounds according to the invention, or which consist of one or more active compounds according to the invention, as well as processes for the preparation of these formulations.

The present invention also includes pharmaceutical formulations in dosage units. This means that the formulations are in the form of individual parts, for example tablets, dragees, capsules, pills, suppositories and ampules of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, a third or a quarter of a daily dose.

By non-toxic, inert pharmaceutically suitable excipients there are to be understood solid, semisolid or liquid diluents, fillers and formulation auxiliaries of every kind.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium bicarbonate, (e) solution retarders, for example paraffin, and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate and magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients can also be in a micro-encapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starches, tragacanth, cellulose derivatives, polyethylene glycols, silicones, bentonites, silica, talc and zinc oxide, or mixtures of these substances.

Powders and sprays can contain, in addition to the active compound or compounds, the customary excipients, for example lactose, talc, silica, aluminum hydroxide, calcium silicate and polyamide powders or mixtures of these substances. Sprays can additionally contain the customary propellants, for example chlorofluorohydrocarbons.

Solutions and emulsions can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerol, glycerol-formal, tetrahydrofurfuryl alcohol, polyethylene glycols and fatty acid esters or sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol esters and sorbitan esters, micro-crystalline cellulose, aluminum metahydroxide, bentonite, agar-agar and tragacanth, or mixtures of these substances.

The formulation forms mentioned can also contain colorants, preservatives and additives which improve the odor and flavor for example peppermint oil and eucalyptus oil, and sweeteners, for example saccharin.

The therapeutically active compounds should preferably be present in the abovementioned pharmaceutical formulations in a concentration of about 0.1 to 99.5, preferably of about 0.5 to 95, % by weight of the total mixture.

The abovementioned pharmaceutical formulations can also contain other pharmaceutical active compounds in addition to the active compounds according to the invention.

The abovementioned pharmaceutical formulations are prepared in the customary manner according to known methods for example by mixing the active compound or compounds with the excipient or excipients.

The present invention also includes the use of the active compounds according to the invention, and of pharmaceutical formulations which contain one or more active compounds according to the invention, in human and veterinary medicine, for the prevention, alleviation and/or cure of the abovementioned diseases.

The active compounds or the pharmaceutical formulations can be administered locally, orally, parenterally, intraperitoneally and/or rectally, preferably parenterally, in particular intravenously and intra-muscularly.

In general, it has proved advantageous both in human medicine and in veterinary medicine, to administer the active compound or compounds according to the invention in total amounts of about 6 to about 800, preferably 15 to 300, mg/kg of body weight every 24 hours, optionally in the form of several, for example 3, individual administrations, in order to achieve the desired results. An individual administration preferably contains the active compound or compounds according to the invention in amounts of about 2 to about 300, in particular 10 to 50, mg/kg of body weight. However, it can be necessary to deviate from the dosages mentioned, and in particular to do so as a function of the species and the body weight of the subject to be treated, the nature and severity of the disease, the nature of the formulation and of the administration of the medicament and the time or interval over which the administration takes place. Thus it can in some cases suffice to manage with less than the abovementioned amount of active compound, while in other cases the abovementioned amount of active compound must be exceeded. The particular optimum dosage required and the type of administration of the active compounds can easily be determined by anyone skilled in the art on the basis of his expert knowledge.

When used as feed additives, the new compounds can be administered in the customary manner together with the feed or with the feed formulations or with the drinking water. By this means, it is possible to prevent an infection by Gram-negative or Gram-positive bacteria and also to achieve better utilization of the feed.

The new $\beta$-lactam antibiotics are distinguished by powerful antibacterial actions, which have been tested in vivo and in vitro, and are capable of being absorbed orally.

In order to broaden the spectrum of action or to achieve a more powerful action, the $\beta$-lactam antibiotics according to the invention can, for example, also be combined with aminoglycoside antibiotics, such as gentamicin, sisomicin, kanamicin, amikacin or tobramicin, and with $\beta$-lactamase inhibitors, such as clavulanic acid, penicillanic acid S-dioxide or olivanic acids.

EXPERIMENTAL SECTION
EXAMPLE 1
1-(3,4-Dihydroxy-benzylideneamino)-2-oxoimidazolidine

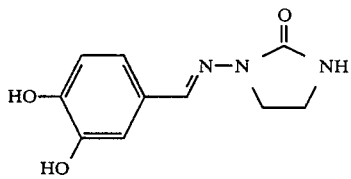
1a.

27.6 g (0.2 mol) of 3,4-dihydroxybenzaldehyde in 100 ml of 80% strength alcohol and 21.2 g (0.208 mol) of aminoimidazolidinone in 100 ml of the same solvent were combined. The product began to crystallize after a few seconds, and was filtered off under suction after 20 minutes, washed with 100 ml of the same solvent and dried over $P_2O_5$ in a desiccator.

Yield: 42.3 g (95.7%). M.p. 260° C.

Calculated: C 54.3, H 5.0, N 19.0, O 21.7 Found: C 54.1, H 5.0, N 18.9, O 21.5.

IR bands at 1687, 1607, 1295, 1278, 1249, 1230, 1200, 1118, 921, 838, 753, 718 cm$^{-1}$.

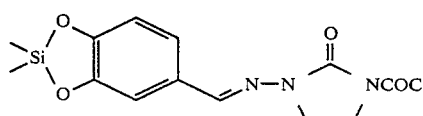
1b.

36.2 g (0.25 mol) of dimethyldichlorosilane and 140 g (0.756 mol) of tributylamine were added to 51.3 g (0.23 mol) of the product from Example 1a in 500 ml of ethyl acetate, and the mixture was kept at 40°-50° C. for 30 minutes and then at 65° C. for a short time until solid materials had substantially dissolved. The mixture was cooled to approximately 5° C., and liquid phosgene (16.8 ml, 0.23 mol) were added, the internal temperature increasing to 28° C. The mixture was then stirred overnight, and the precipitate which separated out was filtered off under suction, rinsed with ethyl acetate and ether, and dried in a desiccator.

M.p. (decomposition)=200° C. Yield 64.7 g (82%).

Calculated: C 46.0, H 4.1, Cl 10.4, N 12.4, Found: C 46.5, H 4.5, Cl 10.4, N 12.0.

IR bands at 1800, 1725, 1255, 1203, 1160, 1102, 953, 900, 814, 730 cm$^{-1}$.

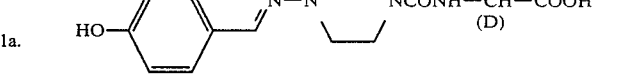
1c.

30 millimols (4.7 g) of D-α-(thien-2-yl)-glycine, 70 millimols (7.7 g) of trimethylchlorosilane, 70 millimols (9.9 ml) of triethylamine and 70 ml of tetrahydrofuran were heated at the boil for two hours, and filtered under suction in the absence of moisture. While cooling with ice, the acid-chloride from Example 1b (30 millimols) was introduced, and stirred with the mixture for 2 hours. 50 ml of water were added, the pH was adjusted to 7, tetrahydrofuran was stripped off in vacuo, the residue was extracted once with ethyl acetate and the aqueous phase was acidified to pH=2 with 1N HCl after 1.8 g of a precipitate had been filtered off under suction. The precipitate was filtered off under suction, washed with water and dried in a desiccator.

Yield 10.6 g (90%).

M.p. (decomposition) 210°-240° C.

Calculated for 98%+2% $H_2O$: C 49.5, H 4.1, N 13.6, S 7.7, Found: C 49.3, H 4.3, N 13.4, S 7.6.

IR bands at 3500-2500, 1715, 1650, 1540, 1275, 1212 cm$^{-1}$.

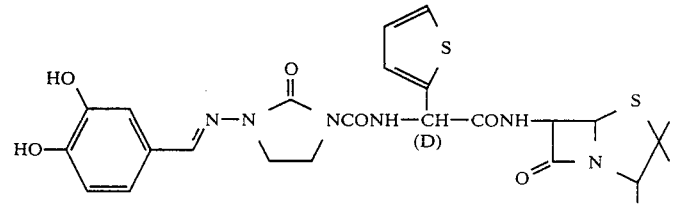
1d.

3.9 g (19 millimols) of the precursor acid from Example 1c in 40 ml of dimethylformamide was stirred with 1.01 g (10 millimols) of N-methylmorpholine for 10 minutes, and the mixture was cooled to −40° C. 1.02 ml (10.6 millimols) of chloroformic acid were then added, and the mixture was allowed to reach −30° C., stirred for 10 minutes at this temperature and cooled again to −55°. A solution, which had been prepared in the meantime and cooled to 0°, of 2.2 g (10 millimols) of 6-aminopenicillanic acid in 10 ml of water (adjusted to pH 7.8 with 1N NaOH) was added in one portion while stirring vigorously, the temperature increasing to −20° to −30° C. The mixture was allowed to reach 0° C. and poured onto 500 ml of water, the pH was adjusted to 7, and the mixture was filtered off under suction from undissolved material (only a very small amount in this case) and acidified with 1N HCl to pH=2. The product was filtered off under suction and introduced into 300 ml of water, and the mixture was again adjusted to pH 7.5 with 2N NaOH (solution), and again acidified with 1N HCl to pH=2. The product was filtered off under suction, washed with water and dried over $P_2O_5$ in a desiccator.

Yield 5.3 g.

IR bands at 3600-2500, 1768, 1716, 1663, 1512, 1277, 1217 cm$^{-1}$.

NMR signals at τ=0.7 (2H), 2.2 (1H), 2.45 (1H), 2.6 (1H), 2.74 (1H), 2.9 (2H), 3.1 (1H), 3.8 (1H), 4.2 (1H), 4.4 (1H), 5.65 (1H), 6.1 (4H), 8.35 (3H) and 8.47 ppm (3H).

EXAMPLE 2

1-Chlorocarbonyl-2-oxo-3-(3,4-dihydroxybenzylideneamino)-imidazolidinone

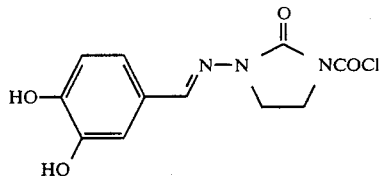
2a.

8.6 g (79 millimols) of trimethylchlorosilane and thereafter 21.3 g (115 millimols) of tributylamine were added to 8 g (36 millimols) of the product from Example 1a in 100 ml of ethyl acetate, in the absence of moisture and while cooling with ice, and the mixture was then heated under reflux, all solid material rapidly going into solution. The mixture was then cooled to 0° C., 3.6 g=2.6 ml (36 millimols) of liquid phosgene were added and the mixture was left to stand overnight, first at 0° C. and then at room temperature. Approximately 60 g of ice were then added while rotating the mixture vigorously, and the precipitate formed was filtered off under suction after 10 minutes, washed with ice water and then with ethyl acetate, and dried over P₂O₅ in a desiccator. 10.3 g. M.p. ~145° C. This product (5 g) was boiled up with 80 ml of acetone. The insoluble precipitate was filtered off under suction and dried. Fraction 1—1. 2 g. M.p. (decomposition)=220° C.

The mother liquor was precipitated with ~100 ml of ether and left to stand at 0° C., and the precipitate was filtered off under suction, washed with ether and dried in vacuo. Fraction 1-2. 1.2 g. M.p. ~142°.

Fraction 1—1: calculated: C 46.6, H 3.6, Cl 12.5, N 14.8, O 22.6, C 47.1, H 4.0, Cl 11.3, N 14.3, O 22.3.

IR bands at 3240, 1780, 1705, 1590, 1283, 1260, 1198, 1160, 1107, 959 and 798 cm⁻¹.

Fraction 1-2: calculated for 55% of product+45% of tributyl hydrochloride: C 54.9, H 7.7, Cl 14.1, N 11.0, O 12.4. found: C 54.9, H 7.4, Cl 13.7, N 10.8, O 12.2.

IR bands at 3250, 3125, 2680, 2640, 1800, 1743, 1598, 1278, 1200, 1163, 1105 and 728 cm⁻¹.

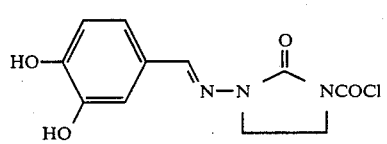
2b.

6 g (27 millimols) of the product from Example 1a were suspended in 54 ml of ethyl acetate at 0° C. in the absence of moisture, 2.2 ml (0.03 mol) of phosgene and 6 g (0.03 mol) of tri-n-butylamine were added and the mixture was stirred at room temperature for 3 hours. The product was filtered off under suction, washed with ethyl acetate and dried.

Yield 5.8 g.

The analysis corresponded to 77.5% of product+21.2% of Bu₃N+1.3% of other products.

calculated: C 51.9, H 5.7, Cl 9.7, N 13.0, found: C 51.9, H 5.5, Cl 9.7, N 13.5.

D-α-[2-oxo-3-(3,4-dihydroxy-benzylideneamino)-imidazolidin-1-yl-carbonylamino]-phenylacetic acid

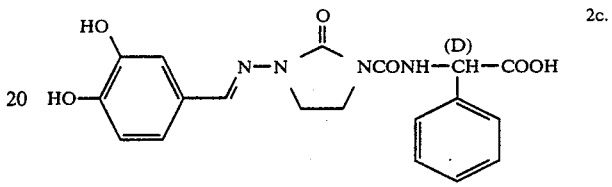
2c.

20 millimols (5.7 g) of the acid-chloride from Example 2a were added to a suspension of 20 millimols (3.02 g) of D-phenylglycine in 30 ml of tetrahydrofuran/H₂O (1:1), and the mixture was kept at pH=8 for 1 hour with 2N NaOH. To complete the reaction, the mixture was then heated at 40°-50° C., at pH=8, for another 30 minutes, and at 70° C. for a further 30 minutes. The mixture was then cooled, and filtered off from 0.2 g of unchanged acid-chloride, and the filtrate was acidified to pH=2 with 5N HCl. The product was filtered off under suction, washed with water and dried. 4.2 g.

Calculated for 77% of product, 21% of 1-(3,4-dihydroxy-benzylideneamino)-2-oxo-imidazolidine+2% of H₂O: C 55.5, H 4.8, N 14.8, found: C 55.5, H 5.2, N 14.2.

The NMR spectrum indicated a weight ratio of 78:22 for the two components.

NMR signals at τ=0.7 (1H), 2.2 (1H), 2.3–2.7 (8H), 2.9 (1H), 3.1 (1H), 4.45 (1H), 6.1 ppm (4H).

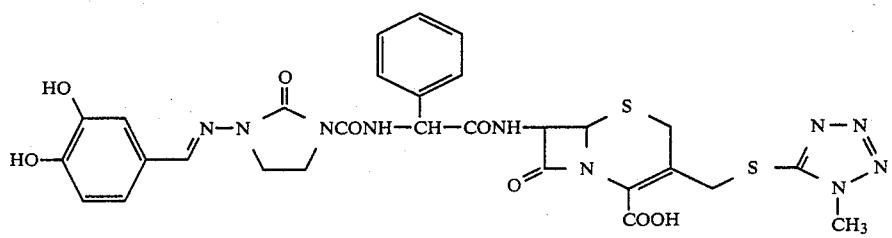
2d.

10 millimols (5.1 g, ~77% strength) of the acid from Example 2c and 3.6 g (11 millimols) of 7-amino-3'-(1-methyl-tetrazol-5-yl-thio)-cephalosporanic acid were reacted as in Example 1d to give a 47% yield.

IR bands at 3600–2400, 1763, 1713, 1656, 1518, 1268, 1218 cm⁻¹.

NMR signals of the sodium salt obtained by freeze-drying the solution of the acid, which had been adjusted to pH=7.5 with NaOH, appeared at τ=2.2 (1H), 2.3–2.8 (6H), 2.9 (1H), 3.1 (1H), 4.15 (1H), 4.25 (1H), 5.03 (1H), 5.4 (1H), 5.7 (1H), 6.0 (3H), 6.1 (4H), 6.35 (1H), 6.5 ppm (1H).

OH signals (broad) at 2.1 and 3.5–7 ppm.

EXAMPLE 3

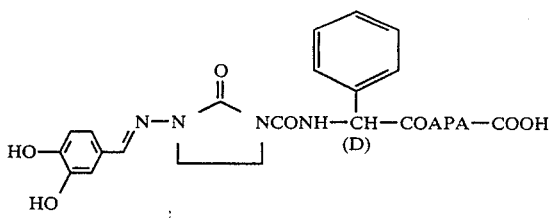

1.4 g (3.5 millimols) of ampicillin trihydrate in 20 ml of 80% strength tetrahydrofuran were reacted, at room temperature and at pH 7 (kept constant with 2N NaOH), with 1 g (3.5 millimols) of the acid-chloride from Example 2b. When the pH remained constant, 30 ml of water were added, the tetrahydrofuran was stripped off, and the residue was washed once with ethyl acetate and then acidified with 2N HCl to pH=2. The precipitated penicillanic acid (0.9 g) was found by thin-layer chromatography to be virtually pure.

IR bands at 3550–2400, 1768, 1715, 1635, 1512, 1269, 1208 cm$^{-1}$.

NMR signals at $\tau$=2.45–2.85 (7H), 3.1 (1H), 3.34 (1H), 4.5 (2H), 4.7 (1H), 5.8 (1H), 6.15–6.5 (4H), 8.6+8.7 ppm (6H).

EXAMPLE 4

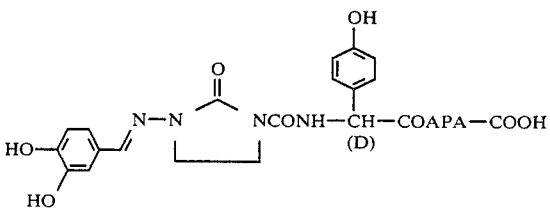

1.5 g (5 millimols) of the acid-chloride from Example 2b, which had been stirred for 5 minutes with ice water and then filtered off under suction, and 1.7 g of amoxicillin trihydrate were reacted as described in Example 3, and the product was isolated as a penicillanic acid. 2.0 g. Virtually pure according to thin-layer chromatography.

IR bands at 3600–2300, 1770, 1715, 1665, 1610, 1512, 1274, 1216 cm$^{-1}$.

NMR signals at $\tau$=2.4–3.4 (8H), 4.4–4.8 (3H), 5.7 (1H), 6.15 (4H), 8.35+8.45 ppm (6H).

EXAMPLE 5

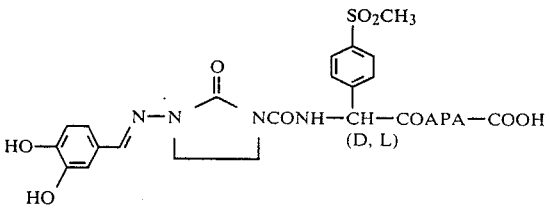

2.0 g (4.8 millimols) of the acid-chloride from Example 2b and 4.6 millimols of D,L-α-amino-4-mesylbenzyl-penicillin were reacted as described in Example 3 to give 2.1 g of the penicillanic acid.

IR bands at 3600–2200, 1770, 1718, 1675, 1517, 1295, 1275, 1215, 1147, 1085, 959, 770 cm$^{-1}$.

NMR signals at $\tau$=2.0 (4H), 2.2 (1H), 2.6 (1H), 2.9 (1H), 3.15 (1H), 3.95 (1H), 4.4+4.5 (2H), 5.75 (1H), 6.1 (4H), 6.8 (3H), 8.5 ppm (6H).

EXAMPLE 6

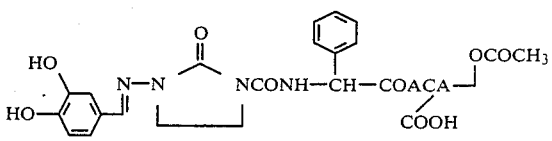

1.3 g (4.6 millimols) of the acid-chloride from Example 2b and 1.86 g (4.6 millimols) of cephaloglycine were converted, as described in Example 3, into the cephalosporanic acid. 2.3 g.

IR bands at 3600–2300, 1770, 1717, 1520, 1270, 1224 cm$^{-1}$.

NMR signals at $\tau$=2.3 (1H), 2.4–2.7 (6H), 2.95 (1H), 3.2 (1H), 4.2 (1H), 4.4 (1H), 4.95+5.0 (2H), 5.23 (1H), 6.0–6.25 (4H), 6.45 (1H), 6.65 (1H), 8.0 ppm (3H).

EXAMPLE 7

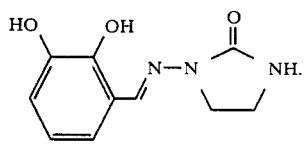
7a

This product was obtained, as described in Example 1a, from 2,3-dihydroxybenzaldehyde and aminoimidazolidinone, in virtually quantitative yield. M.p. ≈260° C.

IR bands at 3400–2500, 1698, 1260, 1160, 730 cm$^{-1}$.
calculated: C 54.3, H 5.0, N 19.0, found: C 54.2, H 5.0, N 18.6.

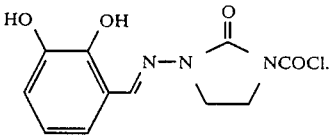
7b 6.05 ml (84 millimols) of phosgene were added to 14.4 g of the product from Example 7a (75 millimols) in 130 ml of ethyl acetate at 0° C., while stirring, after which 15.3 g (83 millimols) of tributylamine were added dropwise in the course of 20 minutes. After the mixture had been stirred for 3 hours, the precipitate was filtered off under suction, washed with ethyl acetate and pressed. It was then stirred with 150 ml of water for approximately 8 minutes, filtered off under suction, washed with water, filtered off rapidly under suction and dried over P$_2$O$_5$ in a vacuum desiccator.

Yield 14 g (66%). Decomposition point 210°–212° C.
Calculated for 98% of product +2% of tributylamine hydrochloride: C 47.0, H 3.8, Cl 12.6, N 13.9, found: C 46.9, H 3.3, Cl 11.8, N 14.1.

IR bands at 3480, 1862, 1832, 1800, 1777, 1708, 1265, 1236, 1188, 1163, 1096, 984, 932, 823, 732 cm$^{-1}$.

1 g (3.5 millimols) of the acid-chloride from Example 7b and 1.43 g (3.5 millimols) of ampicillin trihydrate were reacted as described in Example 8. Yield 1.9 g. According to thin-layer chromatography and NMR, the product is virtually pure.

IR bands at 3600–2400, 1783, 1730, 1664, 1527, 1278, 1240 and 736 cm$^{-1}$.

NMR signals at $\tau=0.7$ (2H), 1.8 (1H), 2.37 (2H), 2.6 (3H), 2.9 (1H), 3.05 (1H), 3.2 (1H), 4.1 (1H), 4.26 (1H), 4.5 (1H), 5.7 (1H), 6.0 (4H), 8.4 (3H) and 8.5 ppm (3H).

EXAMPLE 8

D-α-[2-oxo-3-(3,4-dihydroxy-benzylideneamino)-imidazolidin-1-yl-carbonylamino]-benzylpenicillin

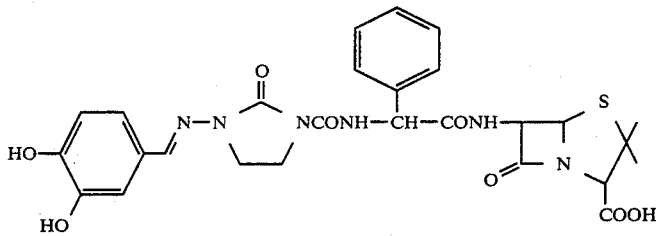

1.43 g (3.5 millimols) of ampicillin trihydrate in 25 ml of 80% strength aqueous tetrahydrofuran were adjusted to pH=7 with 1N NaOH, and 1 g (2.9 millimols) of the acid-chloride from Example 1b were added; the mixture was stirred further, while the pH was kept constant, until no more NaOH was consumed at pH 7. 20 ml of water were then added, tetrahydrofuran was stripped off in vacuo, the residue was extracted once with ethyl acetate and the penicillanic acid was precipitated with 1N HCl, filtered off under suction, suspended in fresh water and brought into solution again at pH=7 using NaOH. The filtered aqueous solution was freeze-dried.

Yield: 1.5 g. Virtually pure according to thin-layer chromatography.

IR bands at 3600–2250, 1768, 1710, 1655, 1517, 1272, 1210 cm$^{-1}$.

NMR signals at $\tau=0.8$ (1H), 2.45 (1H), 2.55 (2H), 2.7 (4H), 3.05 (1H), 3.26 (1H), 4.47 (2H), 4.6 (1H), 5.7 (1H), 6.1–6.35 (4H), 8.5 (3H) and 8.57 ppm (3H).

Calculated 98%+2% of H$_2$O: C 51.4, H 4.6, N 13.3, S 5.1, found: C 51.2, H 5.2, N 13.3, S 5.0.

EXAMPLE 9

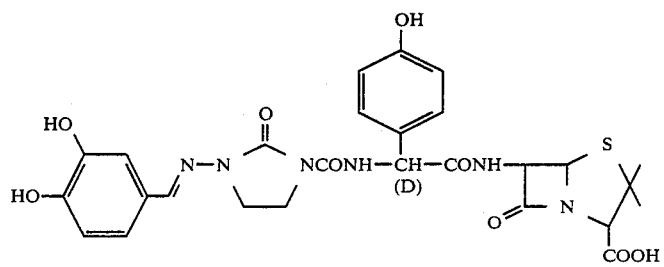

6.4 millimols of the acid-chloride from Example 1b were reacted, as described in Example 8, with 6.4 millimols of amoxicillin trihydrate to give the penicillanic acid. This was brought into solution in water at pH=7 with 2N NaOH, and the solution was filtered and freeze-dried. 3.1 g (76%). Virtually pure according to thin-layer chromatography.

IR bands at 3600–2400, 1770, 1750, 1715, 1650, 1595, 1508, 1270, 1215 cm$^{-1}$.

NMR signals at $\tau=2.65$ (4H), 3.1 (3H), 3.3 (1H), 4.55 (2H), 4.65 (1H), 5.8 (1H), 6.4 (4H), 8.5 (3H) and 8.58 ppm (3H).

EXAMPLE 10

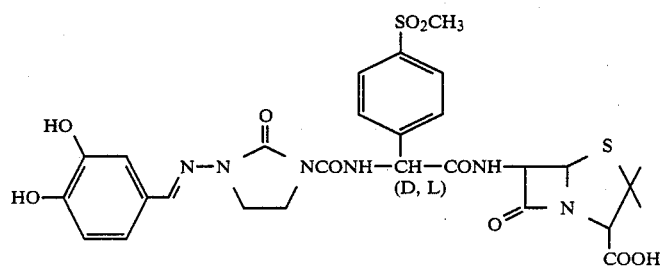

4.8 millimols of the acid-chloride from Example 1b and D,L-p-mesylampicillin were reacted as in Example 8, the solution was filtered off from a neutral precipitate (dihydroxybenzylideneamino-imidazolidinone, 0.9 g), and the product was precipitated as the acid and isolated.

IR bands at 3600–2400, 1770, 1717, 1675, 1617, 1295, 1272, 1215 and 1147 cm$^{-1}$.

NMR signals at $\tau=2.0$ (4H), 2.2 (1H), 2.6 (1H), 2.9 (1H), 3.15 (1H), 3.95 (1H), 4.4+4.5 (2H), 5.75 (1H), 6.1 (4H), 6.8 (3H), 8.5 ppm (6H).

The splitting of the signals at $\tau=5.75$ and 8.5 indicates an approximate 1:1 D,L mixture.

EXAMPLE 11

2.84 g (10 millimols) of the acid-chloride from Example 7b and 4.2 g (10 millimols) of amoxicillin trihydrate were reacted as in Example 8.

Yield 5 g.

IR bands at 3600–2100, 1770, 1715, 1648, 1503, 1270, 1230, 1205, 1170 and 728 cm$^{-1}$.

NMR signals at $\tau=2.0$ (1H), 2.6 (2H), 3.1 (5H), 4.4 (2H), 4.55 (1H), 5.8 (1H), 6.1 (4H), 8.37 (3H) and 8.47 ppm (3H).

EXAMPLE 12

7-D-α-[(2-oxo-3-(3,4-dihydroxybenzylideneamino)-imidazolidin-1-yl)-carbonylamino]-phenylacetamido-cephalosporanic acid 2 g (7 millimols) of the acid-chloride from Example 2a were reacted with 2.8 g (7 millimols) of cephaloglycine, in the manner described in Example 8.

Yield 2.8 g (55%).

Virtually pure according to thin-layer chromatography.

IR bands at 3550–2250, 1770, 1710, 1650, 1517, 1265, 1215, 1104 and 1025 cm$^{-1}$.

NMR signals at $\tau=0.6$ (2H), 2.16 (1H), 2.35 (2H), 2.55 (4H), 2.87 (1H), 3.07 (1H), 4.03 (1H), 4.14 (1H), 4.83 (1H), 4.9 (1H), 5.13 (1H), 6.03 (4H), 6.32 (1H), 6.48 (1H) and 7.9 ppm (3H).

EXAMPLE 13

2.85 g (10 millimols) of the acid-chloride from Example 7b and 4.05 g (10 millimols) of cephaloglycine were reacted as described in Example 8 to give a 26% yield of cephalosporanic acid, which was virtually pure according to thin-layer chromatography, and exhibited IR bands at 3600–2250, 1764, 1718, 1660, 1515, 1232, 1027 and 737 cm$^{-1}$.

After the product had been dissolved in water with NaOH at pH=7.5, and the solution had been freeze-dried, 1.7 g of the corresponding sodium salt were obtained.

IR bands at 3600–2250, 1770, 1718, 1659, 1598, 1520, 1269, 1230, 1028 and 730 cm$^{-1}$.

NMR signals at $\tau=2.0$ (1H), 2.4–2.65 (5H), 2.95–3.3 (3H), 4.2 (1H), 4.37 (1H), 5.0 (2H), 5.13 (1H), 6.1 (4H), 6.48 (1H), 6.75 (1H), 7.95 ppm (3H).

EXAMPLE 14

5.4 g of D-p-hydroxyphenylglycine were reacted, as in the previous example with 7.4 g (26 millimols) of the acid-chloride from Example 2a, and after the reaction was complete the solution was filtered from 3 g of undissolved acid-chloride. After the solution had been acidified, 11.7 g of the acid were obtained.

IR bands at 3550–2000, 1714, 1642, 1538, 1508, 1266, 1210 and 1170 cm$^{-1}$.

NMR signals at τ=0.9 (1H), 2.2 (1H), 2.64 (3H), 2.9 (1H), 3.1 (1H), 4.63 (1H) and 6.1 ppm (4H).

EXAMPLE 16

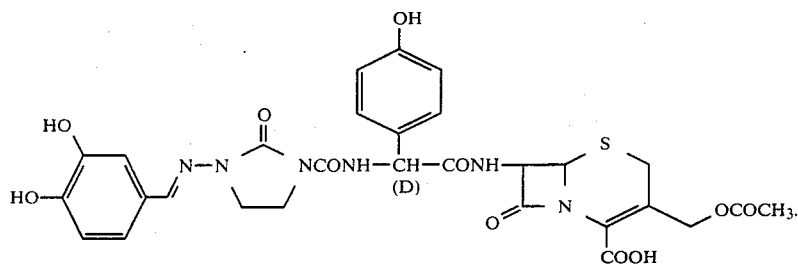

14b 1 g of the acid from Example 14a was reacted, as described in Example 1d, with 2.2 millimols (0.6 g) of 7-aminocephalosporanic acid. Yield: 0.9 g.

IR bands at 3550–2150, 1763, 1710, 1645, 1602, 1508, 1260, 1210, 1168, 1103, 1025, 739 and 719 cm$^{-1}$.

NMR signals at τ=0.8 (2H), 2.2 (1H), 2.6 (3H), 2.9 (1H), 3.1 (3H), 4.2 (1H), 4.3 (1H), 4.9–5.03 (3H), 6.1 (4H), 6.5 (1H), 6.7 (1H), 7.95 (1H), OH signals (broad) at 2.1, 2.6, 5.7 and 6.4 ppm.

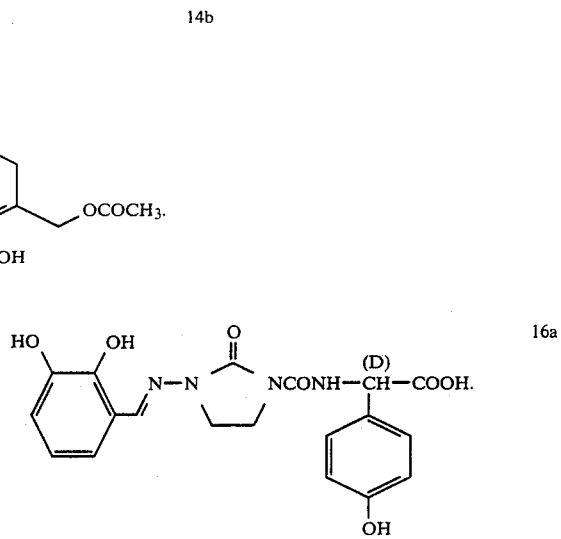

16a

EXAMPLE 15

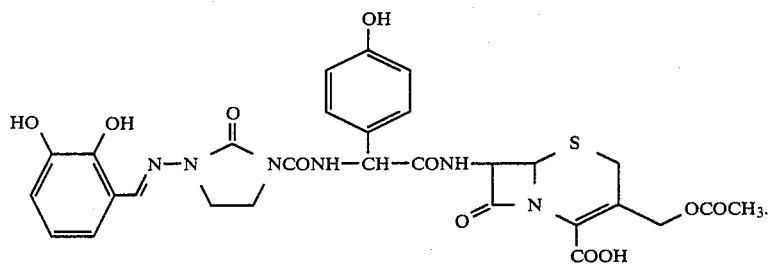

10 millimols of the acid from Example 14a and 11 millimols of 7-amino-3'-(1-methyl-tetrazol-5-yl-thio)-cephalosporanic acid were reacted as described in Example 1d to give a yield of 80% of product.

IR bands at 3600–2250, 1770, 1716, 1652, 1608, 1510, 1265, 1210, 1170, 1100 cm$^{-1}$.

NMR signals at τ=0.8 (2H), 2.15 (1H), 2.6 (3H), 2.9 (1H), 3.1 (3H), 4.1 (1H), 4.3 (1H), 4.85 (1H), 5.55 (2H), 5.9 (3H), 6.05 (4H) and 6.2 ppm (2H).

4.5 g (16 millimols) of the acid-chloride from Example 7b and 2.7 g (16 millimols) of D-p-hydroxyphenylglycine were reacted as in Example 2c, and the solution was filtered off under suction from 0.5 g of unreacted acid-chloride. After the solution had been acidified, 4 g of product were obtained.

IR bands at 3500–2100, 1718, 1650, 1538, 1267, 1168 and 734 cm$^{-1}$.

NMR signals at τ=0.95 (1H), 1.8 (1H), 2.67 (2H), 2.95 (1H), 3.05 (1H), 3.1 (2H), 3.2 (1H), 4.6 (1H) and 6.0 ppm (4H).

16b 2.1 g (5 millimols) of the carboxylic acid from Example 16a and 1.5 g of 7-aminocephalosporanic acid were reacted as described in Example 1d to give 2.9 g of cephalosporanic acid, which was then converted into the freeze-dried Na salt. 2.9 g.

IR bands at 3600–2400, 1770 (shoulder), 1717, 1659, 1559, 1507, 1270, 1235, 1028, 735 cm$^{-1}$.

NMR signals at τ=0.76 (1H), 0.85 (1H), 1.82 (1H), 2.6 (2H), 2.9 (1H), 3.05 (1H), 3.13 (2H), 3.24 (1H), 4.3 (2H), 4.9 (1H), 5.04 (2H), 6.04 (4H), 6.54 (1H), 6.74 (1H) and 7.97 ppm (3H).

EXAMPLE 17

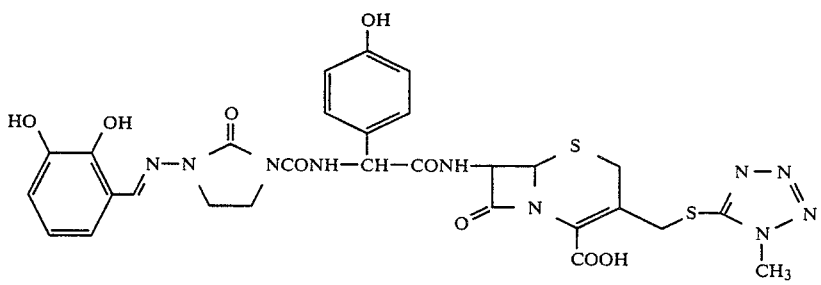

1.7 g (4 millimols) of the carboxylic acid from Example 16a and 1.45 g (4.4 millimols) of 7-amino-3'-(1-methyltetrazol-5-yl-thio)-cephalosporanic acid were reacted as described in Example 1d to give 2.1 g of cephalosporanic acid, which was dissolved again in water at pH=7.5 with NaOH, and again precipitated with HCl. It was then converted into the freeze-dried sodium salt (1.7 g).

IR bands at 3600–2500, 1770 (shoulder), 1722 (s), 1648, 1598, 1518, 1272, 1238, 1168 and 735 cm$^{-1}$.

NMR signals at τ=1.97 (1H), 2.6 (2H), 2.97 (1H), 3.08 (1H), 3.14 (2H), 3.2 (1H), 4.27 (1H), 4.5 (1H), 5.0 (1H), 5.6 (1H), 5.7 (1H), 5.96 (3H), 6.05 (4H), 6.33 (1H) and 6.6 ppm (1H).

EXAMPLE 18

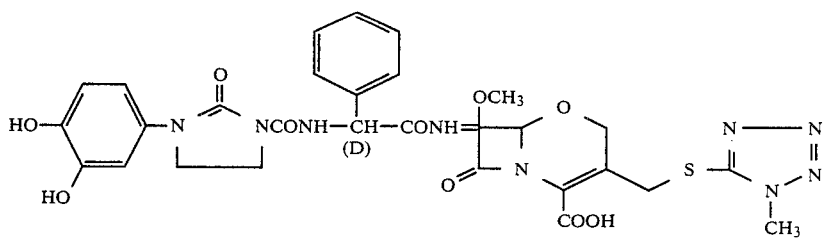

285 mg (1 millimol) of the acid-chloride from Example 7b and 460 mg (1 millimol) of 7β-(D-α-aminophenylacetamido-7α-methoxy-3-(1-methyltertrazol-5-yl-thiomethyl)-1-dethia-1-oxa-cephemcarboxylic acid were reacted in the manner described in Example 8 to give a 32% yield of the 1-dethia-1-oxa-cephalosporin.

IR bands at 3600–2250, 1770, 1720, 1660, 1510 and 740 cm$^{-1}$.

NMR signals at τ=2.1 (1H), 2.4–2.7 (5H), 2.9–3.3 (3H), 4.4 (1H), 4.9 (1H), 5.4–5.8 (4H), 6.0 (3H), 6.1 (4H), 6.6 ppm (3H) (DMF-d$_7$-DMSO-d$_6$).

EXAMPLE 19

341 mg (1 millimol) of the acid-chloride from Example 1b and 460 mg (1 millimol) of 7β-D-α-aminophenylacetamido)-7α-methoxy-3-(1-methyltetrazol-5-yl-thiomethyl)-1-dethia-1-oxa-cephemcarboxylic acid were reacted in the manner described in Example 8 to give a 48% yield of the 1-dethia-1-oxa-cephalosporin.

IR bands at 3500–2200, 1771, 1715, 1662, 1515 and 728 cm$^{-1}$.

NMR signals at τ=2.2 (1H), 2.3–2.8 (6H), 2.9 (1H), 3.1 (1H), 4.2 (1H), 4.85 (1H), 5.3–5.7 (4H), 6.0 (3H), 6.1 (4H), 6.6 ppm (3H).

EXAMPLE 20

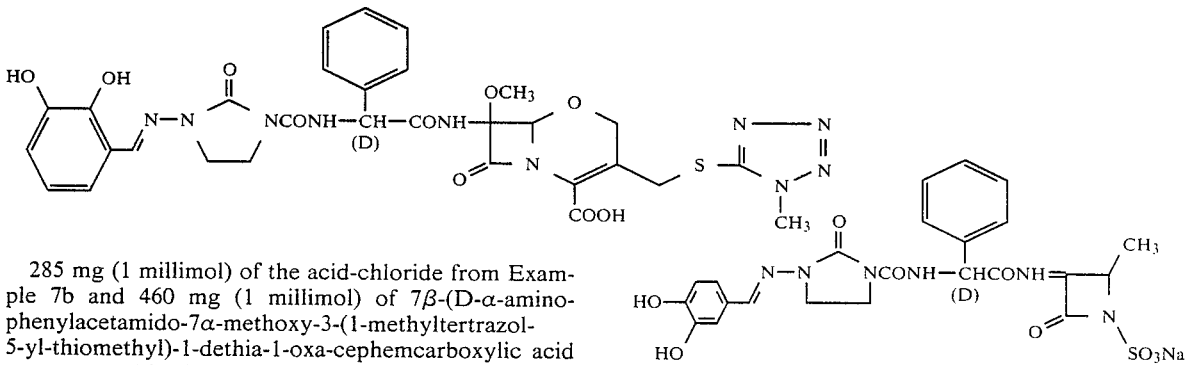

0.8 g (2 millimols) of the acid from Example 2c were reacted, as described in Example 1d, with 400 mg (2.2 millimols) of 3-β-amino-4-α-methyl-azetidin-2-one-1- sulphonic acid, using acetone instead of dimethylformamide, and triethylamine and a little 3-dimethylaminopropanol instead of N-methylmorpholine. Water was added to the reaction solution, the mixture was freed from solvent in vacuo, and the residue was adjusted to pH=3 and filtered off under suction from a precipitate. The aqueous phase was freeze-dried. 0.9 g.

This product was stirred thoroughly with 10 ml of CH$_2$Cl$_2$ for 20 minutes, and the product was filtered off under suction and dried in a desiccator.

IR bands at 3550–2500, 1770, 1755, 1715, 1665, 1620 cm$^{-1}$.

NMR signals at $\tau$=2.3 (1H), 2.45–2.7 (6H), 2.95 (1H), 3.2 (1H), 4.6 (1H), 5.4 (1H), 5.95 (1H), 6.1 (4H) and 8.4 ppm (3H).

EXAMPLE 21

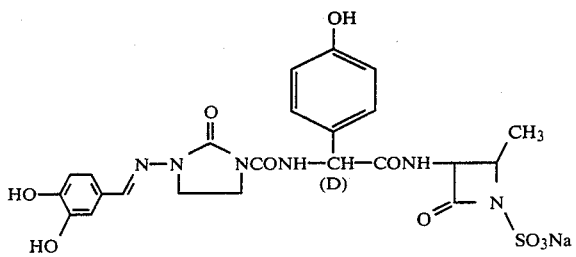

1 g (2.5 millimols) of the acid from Example 14a was reacted, as indicated in Example 20, with 490 mg (2.7 millimols) of 3-β-amino-4-α-methyl-azetidin-2-one-1-sulphonic acid.

Yield 450 mg.

IR bands at 3600–2400, 1755, 1660, 1510 and 1042 cm$^{-1}$.

NMR signals at $\tau$=2.3 (1H), 2.7 (3H), 2.9 (1H), 3.2 (3H), 4.5 (1H), 5.25 (1H), 5.9 (1H), 6.1 (4H), 8.4 ppm (3H).

EXAMPLE 22

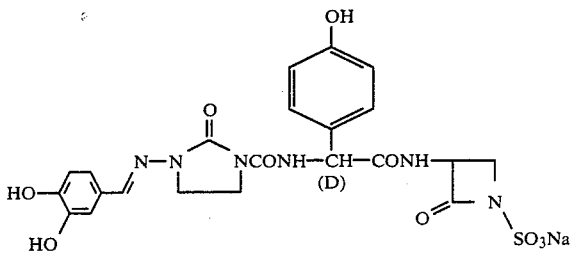

1 g (2.5 millimols) of the acid from Example 14a was reacted, as indicated in Example 20, with 2.7 millimols (450 mg) of 3-β-amino-azetidin-2-one-1-sulphonic acid.

Yield: 450 mg.

IR bands at 3600–2300, 1770, 1755, 1657, 1042 cm$^{-1}$.

NMR signals at $\tau$=2.3 (1H), 2.6–2.7 (3H), 2.9 (1H), 3.1–3.2 (3H), 4.5 (1H), 5.1 (1H), 6.0–6.2 (5H) and 6.4 ppm (1H).

EXAMPLE 23

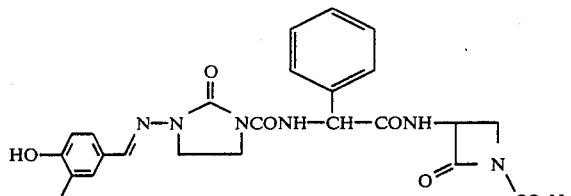

0.8 g (2 millimols) of the acid from Example 2c were reacted, as indicated in Example 20, with 365 mg (2.2 millimols) of 3-β-amino-azetidin-2-one-1-sulphonic acid.

Yield: 0.6 g.

IR bands at 3600–2300, 1770, 1757, 1717, 1660, 1520 and 1044 cm$^{-1}$.

NMR signals at $\tau$=2.3 (1H), 2.45–2.7 (6H), 2.95 (1H), 3.2 (1H), 4.5 (1H), 5.1 (1H), 6.0–6.2 (5H) and 6.4 ppm (1H).

It is understood that the specification and examples are illustrative but not limitative of the present invention and that other embodiments within the spirit and scope of the invention will suggest themselves to those skilled in the art.

EXAMPLE 24

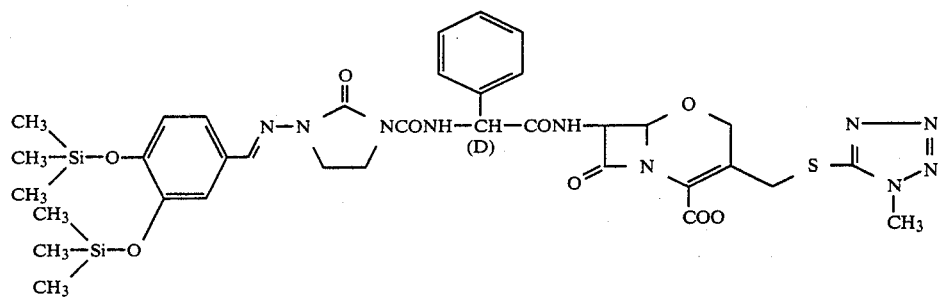

479 mg (0.88 mM, 1.3 äqu.) disilylated precursor acid of example 2 c in 2.8 ml dry methylene chloride were cooled under a nitrogen atmosphere to 0° C., then 116 mcl (1.06 mM, 1.56 äqu.) of N-methyl morpholin were added and after stirring for 3 min. the mixture was cooled to −35° C. Then 163 mcl (0.97 mM, 1.43 äqu.) of trifluoro methanesulfonic acid anhydride were added and the mixture was stirred for 20 min. at this temperature (solution A).

In the meantime 325 mg (0.68 mM) of 7-amino-1-dethia-1-oxa-3'-desacetoxy-3'-(1-methyl-tetrazol-5-yl)-thio-cephalosporanic acid benzhydrylester and 0.75 mM (1.1 äqu.) N-methyl-morpholin were dissolved in 2.2 ml CH$_2$Cl$_2$ and this solution was added to the −55° C. cold solution A.

The mixture was allowed to warm up to −20° C. and was then poured into an aqueous solution which was overlayered with CHCl₃ under vigorous stirring. The organic extract was shortly washed with water, dried over MgSO₄ and the solvent was evaporated.

Yield: 168 mg (25%)

NMR-signals at δ=9,1 (1H), 7,54 (1H), 7,5 (1H), 7,45–7,15 (17H), 6,85 (1H), 6,8 (2H), 5,7 (1H), 5,5 (1H), 5,0 (1H), 4,65 (1H), 4,45 (1H), 4,24 (2H), 4,0 (2H), 3,77 (5H) and 0,3 ppm (18H) (in CDCl₃).

IR-absorption at 3300, 3065, 3035, 2961, 1796, 1730, 1678, 1510, 1410, 1254, 910, 844, 746, 698 cm⁻¹ (in KBr).

EXAMPLE 25

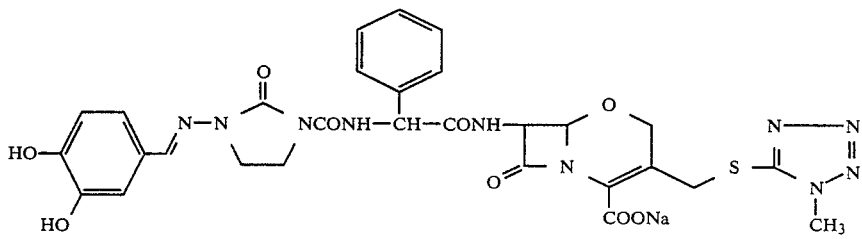

151 mg of the product of example 24 in 6 ml CH₂Cl₂ at 0° C. were stirred with 3 ml anisole and 3 ml trifluoro acetic acid for 30 min. Then water was added, the CH₂Cl₂-layer separated the aqueous phase was treated with a few milliliters of CH₂Cl₂ and the combined organic phase were washed with water. It was dried with MgSO₄ and the trifluoro acetic acid and methylene chloride were removed under vacuum. Then again CH₂Cl₂ was added and the product was extracted in water by adding 1 n NaOH so as to adjust the pH to 7. The aqueous phase was freeze dried.

Yield 98 mg=91%.

IR-absorption at 1771, 1725, 1668, 1604, 1528, 1458, 1417, 1274, 1103 and 1023 cm⁻¹ (in KBr).

NMR-signals at δ=9,14 (1H), 9,05 (1H), 7,6 (1H), 7,45–7,3 (5H), 7,16 (1H), 6,9 (1H), 6,73 (1H), 5,62 (1H), 5,35 (1H), 4,9 (1H), 4,45 (1H), 4,32 (1H), 4,1 (1H), 3,9 (3H) and 3,76 ppm (4H).

We claim:

1. A compound of the formula

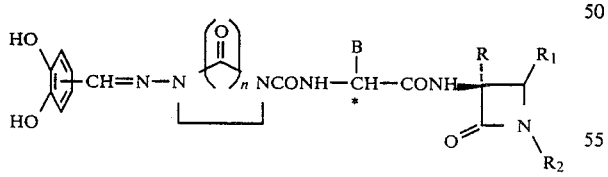

in which
B represents optionally substituted phenyl or cyclohexadienyl, or an unsaturated, optionally substituted heterocyclic ring;
R represents hydrogen or methoxy;
n is 1 or 2;
R₁ is hydrogen or optionally substituted alkyl;
R₂ is SO₃⊖M⊕; and
M⊕ is a proton or a cation;
or R₁ and R₂, together with the azetidinone ring to which they are bonded, represent

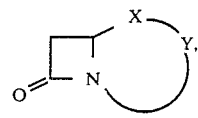

wherein
X represents S, O, SO, SO₂ or CH₂; and
Y represents

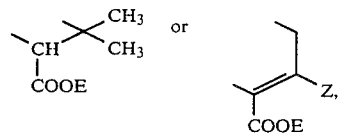

in which the carbon atom which carries the —COOE group is bonded to the nitrogen atom of the β-lactam ring, and
Z represents hydrogen, halogen, alkoxy or —CH₂—T,
T denotes hydrogen, alkyl-CO—O—, pyridinium, carboxamidopyridinium, aminopyridinium, carbamoyloxy, azido, cyano, hydroxyl, the group —S—phenyl which can be substituted, or the group —S—het, in which het represents an optionally substituted 5-membered or 6-membered heterocyclic ring;
and wherein
E represents hydrogen, a pharmaceutically usable ester grouping, a salt-forming cation or a suitable protective group;
or a hydrate thereof.

2. A compound or hydrate according to claim 1, in which
B is phenyl which is unsubstituted or monosubstituted or disubstituted by methyl, ethyl, aminomethyl, hydroxyl, methoxy, ethoxy, carbamoyloxy, acetoxy, amino, mesylamino, methylamino, aminosulphonylamino, guanidyl, carbamoylamino, carboxyl, methoxycarbonyl, carbamoyl, amidino, mesyl, methylsulphinyl, sulpho, methylthio or halogen, or is an unsaturated 5-membered or 6-membered heterocyclic structure which has 1 to 4 heteroatoms, contains oxygen, nitrogen or sulphur atoms in the ring, and is unsubstituted or monosubstituted or disubstituted by methyl, ethyl, hydroxyl, oxo, amino, imino, mesyl, mesylamino, carboxyl, carbamoyl or acetyl,
R denotes hydrogen or methoxy,
n denotes 1,
R₁ denotes straight-chain or branched alkyl which has up to 5 C atoms, may be unsaturated or cyclized, and can be substituted by hydroxyl, amino, carboxyl, carbamoyl or mesyl, $R_2$ denotes $SO_3^{\ominus}M^{\oplus}$, wherein $M^{\oplus}$ denotes an alkali metal cation or alkaline earth metal cation, the aluminum cation or the ammonium ion, a protonated primary, secondary or tertiary aliphatic amine, or a heterocyclic amine, or $R_1$ and $R_2$, together with the azetidinone ring to which they are bonded, represent

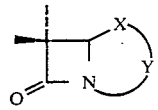

Z represents hydrogen, halogen, methoxy,, ethoxy, n-propoxy and i-propoxy or —$CH_2$—T, and T denotes hydrogen, acetate, propionate, n-butyrate or i-butyrate which can be substituted by carboxyl, hydroxyl or amino, or denotes pyridinium, carboxamidopyridinium, aminopyridinium, carbamoyloxy, azido, cyano, hydroxyl or the group —S—phenyl which can be substituted by methyl, halogen, amino, hydroxyl or carboxyl, or denotes the group —S—het, in which het represents a 5-membered or 6-membered heterocyclic structure which has 1–4 heteroatoms, contains oxygen, nitrogen or sulphur atoms in the ring, and can be unsubstituted or monosubstituted or disubstituted by alkyl which can be substituted by carboxyl, sulpho, amino, methylamino, dimethylamino or hydroxyl and has up to 3 C atoms or by hydroxyl, oxo, amino, imino or sulpho.

3. A compound or hydrate according to claim 2, in which

B is phenyl which is unsubstituted or monosubstituted or disubstituted by methyl, ethyl, aminomethyl, hydroxyl, ethoxy, carbamoyloxy, acetoxy, amino, mesylamino, methylamino, aminosulphonyl-amino, guanidyl, carbamoylamino, carboxyl, methoxy-carbonyl, carbamoyl, amidino, mesyl, methyl-sulphinyl, sulpho, methylthio or halogen, or is a furyl, methylfuryl, thienyl, methylthienyl, 2-aminothiazolyl, thiazolyl, methylisoxazolyl, isoxazolyl, pyridyl, 2-aminopyrimidyl, thiadiazolyl, pyranyl, thiapyranyl or sydnonyl ring, and T denotes hydrogen, acetate, propionate, n-butyrate or i-butyrate which can be substituted by carboxyl, hydroxyl or amino, or denotes pyridinium, carboxamidopyridinium, aminopyridinium, carbamoyloxy, azido, cyano, hydroxyl, or the group —S—phenyl which can be substituted by methyl, halogen, amino, hydroxyl or carboxyl, or denotes the group —S—het in which het denotes a thiazole, isothiazole, thiadiazolyl, thiazolyl or tetrazolyl ring, each of which is unsubstituted or substituted by methyl, sulphomethyl, carboxymethyl or dimethylaminoethyl, or denotes the pyridyl, 1-oxidopyridyl, 2-methyl-5-oxo-6-hydroxy-1,4-dihydro-1,2,4-triazine or 4-formylmethyl-5-oxo-6-hydroxy-4,5-dihydro-1,2,4-triazinyl ring.

4. A compound according to claim 1, wherein such compound is

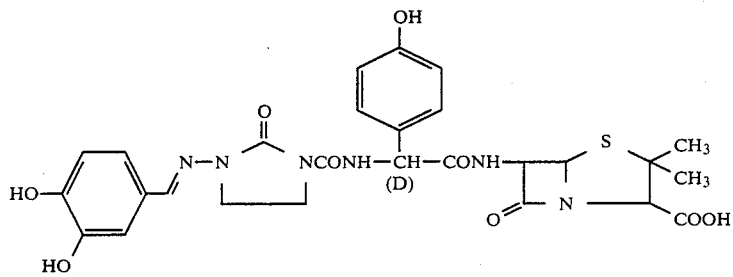

or a hydrate thereof.

5. A compound according to claim 1, wherein such compound is

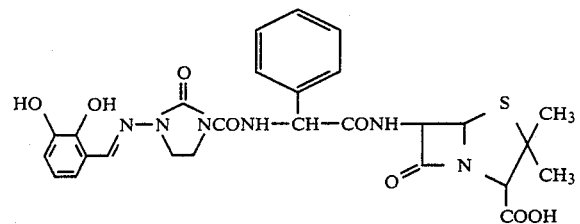

or a hydrate thereof.

6. A compound according to claim 1, wherein such compound is

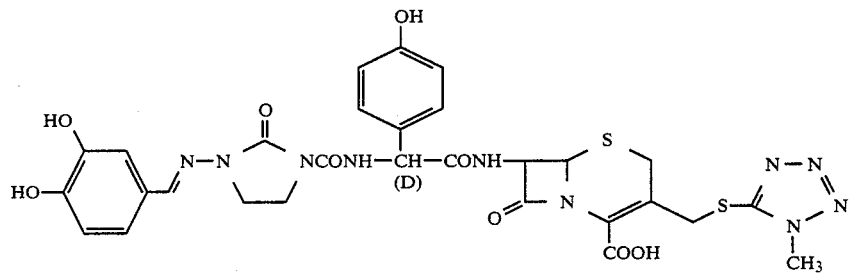

or a hydrate thereof.

7. A compound according to claim 1, wherein such compound is

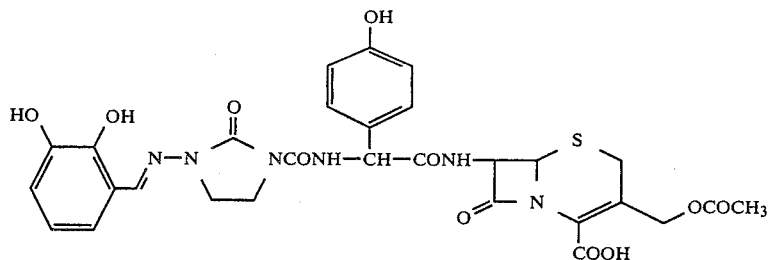

or a hydrate thereof.

8. A compound according to claim 1, wherein such compound is

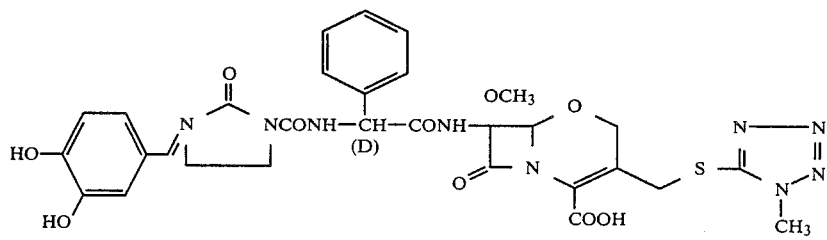

or a hydrate thereof.

9. A compound according to claim 1, wherein such compound is

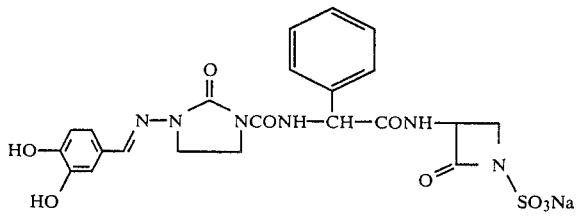

or a hydrate thereof.

10. An antibiotically active composition comprising an antibiotically active amount of a compound according to claim 1 in admixture with a diluent.

11. A composition according to claim 10 in the form of a tablet, capsule or pill containing a unit dose.

12. A method of combating bacteria which comprises administering to such bacteria or a bacteria habitat a bactericidally effective amount of a compound according to claim 1.

13. The method according to claim 12, wherein such compound is

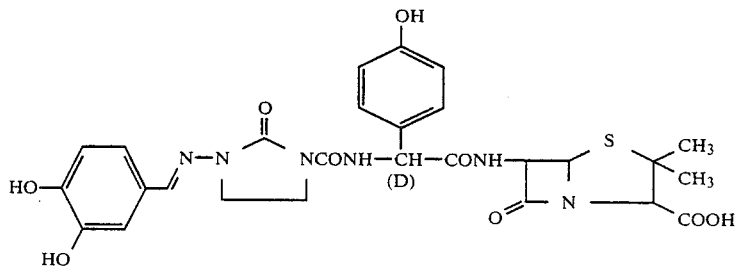

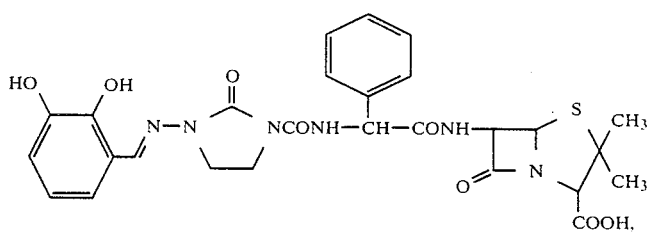

-continued

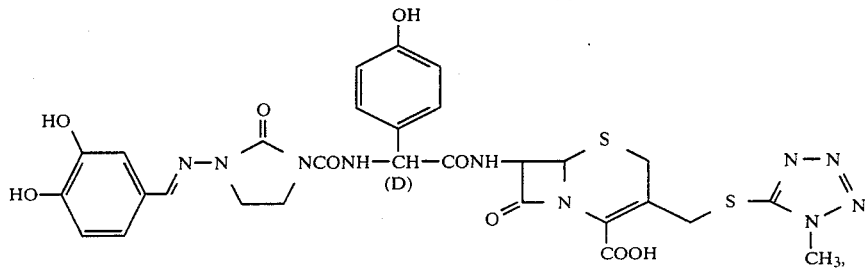

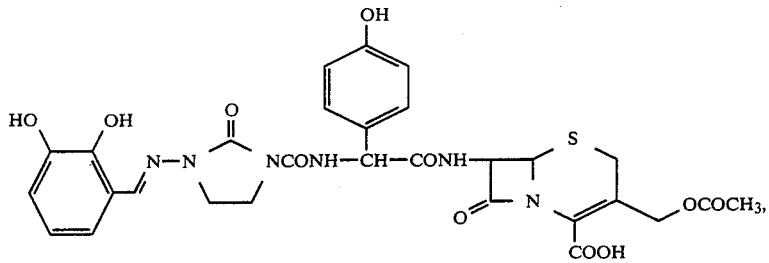

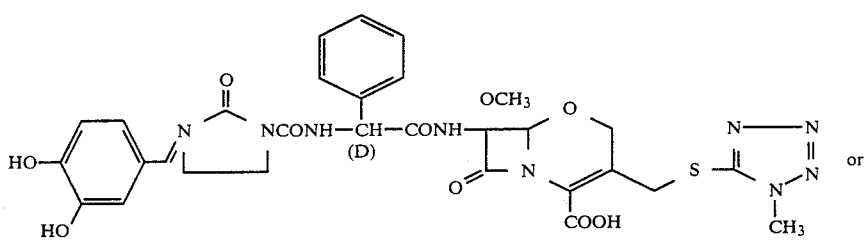

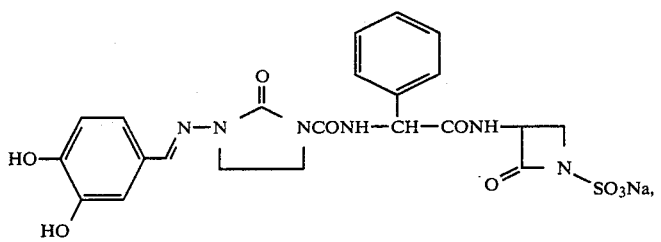

or a hydrate thereof.

14. The method according to claim 12, wherein such compound or hydrate is administered to a patient.

15. The method according to claim 12, wherein such compound or hydrate is administered to a patient infected with Pseudomonas bacteria.

16. The method of preserving a substrate against attack by microorganisms which comprises applying thereto a preservative amount of a compound according to claim 1.

17. A method of promoting the growth of an animal which comprises using a feed containing a growth promoting effective amount of a compound according to claim 1.

18. An animal feed containing a growth promoting effective amount of a compound according to claim 1.

* * * * *

UNITED STATES PATENT AND TRADEMARK OFFICE
CERTIFICATE OF CORRECTION

PATENT NO. : 4,515,789     Page 1 of 3

DATED : May 7, 1985

INVENTOR(S) : Karl G. Metzger, et al.

It is certified that error appears in the above-identified patent and that said Letters Patent is hereby corrected as shown below:

| | |
|---|---|
| Col. 4, line 17, Col. 8, line 36 and Col. 10, line 2 | Delete "C" and substitute --C_*-- |
| Col. 4, line 32 | After "solvents" insert --or (c) water and one or more organic solvents-- |
| Col. 6, line 63 | Delete lower left of structure and substitute 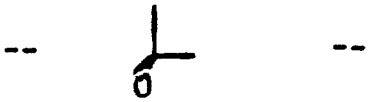 |
| Col. 7, line 62 | Delete "relative" and substitute --reactive-- |
| Col. 8, line 10 | End of structure delete "-B-/-CH-" and substitute --B/-CH_*--  |
| Col. 8, line 10 and Col. 8, line 30 | End of structure delete " " and substitute 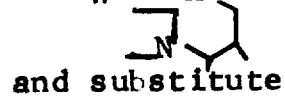 |
| Col. 9, line 10 | Delete middle of structure and substitute 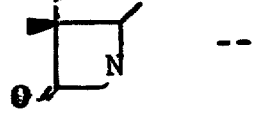 |

UNITED STATES PATENT AND TRADEMARK OFFICE
CERTIFICATE OF CORRECTION

PATENT NO. : 4,515,789

DATED : May 7, 1985

INVENTOR(S) : Karl G. Metzger, et al.

It is certified that error appears in the above-identified patent and that said Letters Patent is hereby corrected as shown below:

| | |
|---|---|
| Col. 10, line 20, Col. 11, line 1 and Col. 13, line 1 | Delete end of structure and substitute 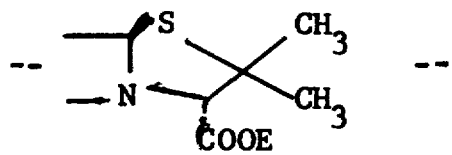 |
| Col. 24, 4th structure under Column "Z" | Delete N ⊕ " and substitute -- N ⊖ -- |
| Col. 28, line 48 | Delete "Agalactiae" and substitute --agalactiae-- |
| Col. 29, line 8 | Correct spelling of Pseudomonadaceae" |
| Col. 29, lines 8,9 | Correct spelling of "pseudomallei" |
| Col. 30, Ex. 7c, last 2 columns; Col. 30, Ex. 4, last column; Col. 30, Ex. 2d, 5th column; Col. 30, Ex. 15, last column and Col. 32, last 2 columns | Delete " ≦ " and substitute -- ≦ -- |
| Col. 33, line 49 | After "esters" delete "or" and substitute --of-- |
| Col. 44, line 32 | Delete "3600 - 2250" and substitute --3600 - 2500-- |
| Col. 47, line 63 | Correct spelling of "methyltetrazol" |

UNITED STATES PATENT AND TRADEMARK OFFICE
CERTIFICATE OF CORRECTION

PATENT NO. : 4,515,789

DATED : May 7, 1985

INVENTOR(S) : Karl G. Metzger, et al.

It is certified that error appears in the above-identified patent and that said Letters Patent is hereby corrected as shown below:

Col. 52, line 1    Delete beginning of structure and substitute

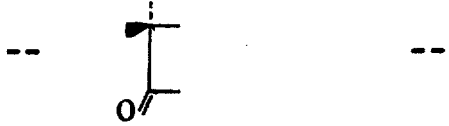

Col. 57, middle of 3rd structure    Insert -- -- as follows:

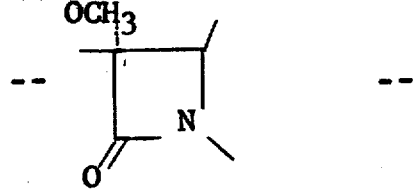

𝔖igned and 𝔖ealed this

Fourth Day of February 1986

[SEAL]

Attest:

DONALD J. QUIGG

Attesting Officer    Commissioner of Patents and Trademarks